US007576095B2

(12) United States Patent
Cheng

(10) Patent No.: US 7,576,095 B2
(45) Date of Patent: Aug. 18, 2009

(54) THERAPEUTIC AGENTS

(75) Inventor: Leifeng Cheng, Gothenburg (SE)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 11/730,640

(22) Filed: Apr. 3, 2007

(65) Prior Publication Data
US 2008/0009513 A1    Jan. 10, 2008

Related U.S. Application Data

(63) Continuation-in-part of application No. PCT/GB2006/003695, filed on Oct. 5, 2006.

(60) Provisional application No. 60/724,156, filed on Oct. 6, 2005.

(51) Int. Cl.
*A61K 31/437* (2006.01)
*A61P 1/00* (2006.01)
*A61P 11/00* (2006.01)
*A61P 25/00* (2006.01)
*A61P 25/16* (2006.01)
*A61P 25/18* (2006.01)
*A61P 25/22* (2006.01)
*A61P 25/24* (2006.01)
*A61P 25/28* (2006.01)
*A61P 25/30* (2006.01)
*A61P 3/04* (2006.01)
*A61P 5/00* (2006.01)
*C07D 471/04* (2006.01)

(52) U.S. Cl. .................................. 514/300; 546/113
(58) Field of Classification Search ........................ None
See application file for complete search history.

(56) References Cited

U.S. PATENT DOCUMENTS

| | | | |
|---|---|---|---|
| 5,462,960 A | 10/1995 | Barth et al. | |
| 5,624,941 A | 4/1997 | Barth et al. | |
| 6,344,474 B1 | 2/2002 | Maruani et al. | |
| 2004/0038980 A1* | 2/2004 | Lam et al. | 514/252.04 |

FOREIGN PATENT DOCUMENTS

| WO | WO 01/70700 | 9/2001 |
|---|---|---|
| WO | WO 03/027114 | 4/2003 |
| WO | WO 2005/080328 | 9/2005 |
| WO | WO 2005/080343 | 9/2005 |
| WO | WO 2005/095354 | 10/2005 |

OTHER PUBLICATIONS

Wermuth, Camille G: The Practice of Medicinal Chemistry, Academic Press Limited, 1996, p. 204-228.*
Xie et al., J Clin Pharm Thera, 32 (3): 209-231, 2007.*
Marzo, Rrug Discovery Today, 13:1026-1041, 2008.*
Hertzog "Recent advances in the cannabinoids" Expert Opinion on Therapeutic Patents 14(10):1435-1452 (2004).
Katoch-Rouse et al. "Synthesis, structure-activity relationship, and evaluation of. SR141716 analogues: Development of central cannabinoid receptor ligands with lower lipophilicity" Journal of Medicinal Chemistry 46(4):642-645 (2003).
Lange et al. "Bioisosteric Replacements of the Pyrazole Moiety of Rimonabant: Synthesis, Biological Properties, and Molecular Modeling Investigations of Thiazoles, Triazoles, and Imidazoles as Potent and Selective CB1 Cannabinoid Receptor Antagonists" Journal of Medicinal Chemistry 48:1823-1838 (2005).
Palmer et al. "Cannabinergic ligands" Chemistry and Physics of Lipids 121:3-19 (2002).
Smith et al. "Constrained analogs of CB-1 antagonists: 1,5,6,7-Tetrahydro-4H-pyrrolo[3,2-c]pyridine-4-one derivatives" Bioorganic & Medicinal Chemistry Letters 17(3): 673-678 (2007).
Smith et al. "Constrained analogs of CB-1 antagonists for the treatment of obesity: Design, synthesis, and pharmacology of 1,5,6,7-tetrahydro-4H-pyrrolo[3,2-c]pyridin-4-one derivatives" Advance Notice of Presentation by R.A. Smith at 230th ACS National Meeting, in Washington DC, Aug. 28-Sep. 1, 2005.
Notes taken by AstraZeneca employee Lanna Li at presentation by R.A. Smith at 230th ACS National Meeting, in Washington DC, Aug. 28-Sep. 1, 2005.

* cited by examiner

*Primary Examiner*—Brian-Yong S Kwon
*Assistant Examiner*—Bong-Sook Baek
(74) *Attorney, Agent, or Firm*—Morgan Lewis & Bockius LLP

(57) ABSTRACT

The present invention relates to 4,5-dihydropyrrolo[3,2-c]pyridin-4-one compounds of formula IA and processes for preparing such compounds, their use in the treatment of obesity, psychiatric and neurological disorders, to methods for their therapeutic use and to pharmaceutical compositions containing them.

3 Claims, No Drawings

THERAPEUTIC AGENTS

RELATED APPLICATIONS

This application is a continuation in part of international application PCT/GB2006/003695 filed Oct. 5, 2006, which in turn claims priority to U.S. provisional application No. 60/724,156 filed Oct. 6, 2005.

FIELD OF INVENTION

The present invention relates to certain 4,5,6,7-tetrahydropyrrolo[3,2-c]pyridin-4-one and 4,5-dihydropyrrolo[3,2-c]pyridin-4-one compounds of formula I, to processes for preparing such compounds, to their use in the treatment of obesity, psychiatric and neurological disorders, to methods for their therapeutic use and to pharmaceutical compositions containing them.

BACKGROUND OF THE INVENTION

It is known that certain $CB_1$ modulators (known as antagonists or inverse agonists) are useful in the treatment of obesity, psychiatric and neurological disorders (WO 01/70700 and EP 656354). WO03/027114 discloses the use of 1,5,6,7-tetrahydropyrrolo[3,2-c]pyridine and 1,5,6,7-tetrahydropyrrolo[3,2-c]pyridin-4-one derivatives for the treatment of obesity. However, there is a need for $CB_1$ modulators with improved physicochemical properties and/or DMPK properties and/or pharmacodynamic properties.

DESCRIPTION OF THE INVENTION

The present invention provides a compound of formula I

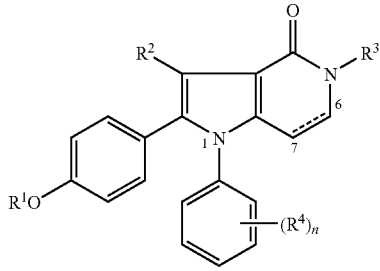

I wherein $R^1$ represents a $C_{3-7}$ alkyl group substituted by one or more fluoro or $R^1$ represents a $C_{1-7}$ alkylsulphonyl group substituted by one or more fluoro;
$R^2$ represents cyano, or a $C_{1-4}$ alkyl group optionally substituted by hydroxy or by a group $NR^aR^b$ in which $R^a$ and $R^b$ independently represent H or a $C_{1-3}$alkyl group;
$R^3$ represents piperidin-1-yl or cyclohexyl each of which is optionally substituted by one or more groups selected from hydroxy, fluoro or a group $NR^cR^d$ in which $R^c$ and $R^d$ independently represent H or a $C_{1-3}$ alkyl group; and
- - - is an optional additional bond between positions 6 and 7;
$R^4$ represents chloro, fluoro, cyano or methyl;
n is 1, 2 or 3 and each $R^4$ is independently selected when n>1;
and pharmaceutically acceptable salts thereof.

In another aspect the present invention provides a compound of formula IA

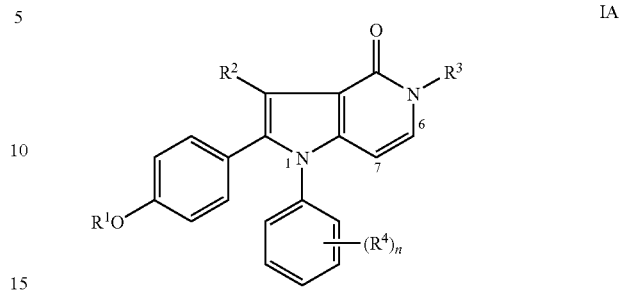

IA wherein $R^1$ represents a $C_{3-7}$ alkyl group substituted by one or more fluoro or $R^1$ represents a $C_{1-7}$ alkylsulphonyl group substituted by one or more fluoro;
$R^2$ represents cyano, or a $C_{1-4}$ alkyl group optionally substituted by hydroxy or by a group $NR^aR^b$ in which $R^a$ and $R^b$ independently representsH or a $C_{1-3}$alkyl group;
$R^3$ represents piperidin-1-yl or cyclohexyl each of which is optionally substituted by one or more groups selected from hydroxy, fluoro or a group $NR^cR^d$ in which $R^c$ and $R^d$ independently represent H or a $C_{1-3}$ alkyl group; and
$R^4$ represents chloro, fluoro, cyano or methyl;
n is 1, 2 or 3 and each $R^4$ is independently selected when n >1;
and pharmaceutically acceptable salts thereof.

In another aspect the present invention provides a compound of formula IB

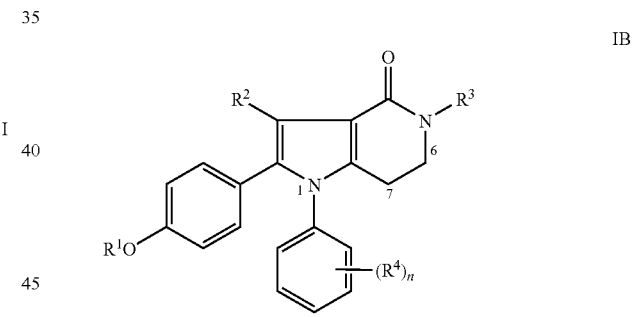

IB wherein $R^1$ represents a $C_{3-7}$alkyl group substituted by one or more fluoro or $R^1$ represents $C_{1-7}$alkylsulphonyl group substituted by one or more fluoro;
$R^2$ represents cyano, or a $C_{1-4}$ alkyl group optionally substituted by hydroxy or by a group $NR^aR^b$ in which $R^a$ and $R^b$ independently represent H or a $C_{1-3}$alkyl group;
$R^3$ represents piperidin-1-yl or cyclohexyl each of which is optionally substituted by one or more groups selected from hydroxy, fluoro or a group $NR^cR^d$ in which $R^c$ and $R^d$ independently represent H or a $C_{1-3}$alkyl group; and
$R^4$ represents chloro, fluoro, cyano or methyl;
n is 1, 2 or 3 and each $R^4$ is independently selected when n>1;
and pharmaceutically acceptable salts thereof.

Further values of $R^1$, $R^2$, $R^3$ and $R^4$ in compounds of formula I, formula IA and IB now follow. It will be understood that such values may be used where appropriate with any of the definitions, claims or embodiments defined hereinbefore or hereinafter.

Suitably $R^1$ represents a $C_{1-7}$alkylsulphonyl group substituted by one or more fluoro for example, 4,4,4-trifluorobutyl-1-sulfonyl, 4-fluorobutyl-1-sulfonyl, 3,3,3-trifluoropropyl-1-sulfonyl, or 3-fluoropropyl-1-sulfonyl. Suitably $R^1$ represents a $C_{3-7}$alkyl group substituted by one or more fluoro for example 4,4,4-trifluorobutyl, 4-fluorobutyl, 3,3,3-trifluoropropyl or 3-fluoropropyl. More particularly $R^1$ represents a $C_{3-5}$alkylsulphonyl group terminally substituted by one or more fluoro.

Suitably $R^2$ represents cyano, or a $C_{1-4}$alkyl group optionally substituted by hydroxy for example methyl, ethyl or hydroxymethyl or a $C_{1-4}$alkyl group optionally substituted by a group $NR^aR^b$ in which $R^a$ and $R^b$ independently represent H or a $C_{1-3}$alkyl group for example aminomethyl, methylaminomethyl or dimethylaminomethyl. Particularly $R^2$ represents methyl or hydroxymethyl. More particularly $R^2$ represents methyl.

Suitably $R^3$ represents piperidin-1-yl or cyclohexyl each of which is optionally substituted by one or more groups selected from hydroxy, fluoro or a group $NR^cR^d$ in which $R^c$ and $R^d$ independently represent H or a $C_{1-3}$alkyl group for example 4-hydroxypiperidin-1-yl, 2-hydroxycyclohexyl, 3-hydroxycyclohexyl, 4-hydroxycyclohexyl, 2-aminocyclohexyl, 3-aminocyclohexyl, 2-dimethylaminocyclohexyl, 3-dimethylaminocyclohexyl or 4,4-difluorocyclohexyl. Particularly $R^3$ represents piperidin-1-yl.

Suitably $R^4$ represents chloro, fluoro, cyano or methyl and n is 1, 2 or 3 for example 2,4-dichloro, 2-chloro, 2-methyl, 2-cyano, 3-cyano, 4-cyano, 3-fluoro-5-cyano or 2-methyl-4-chloro. Particularly $R^4$ represents 2-chloro when n is 1 or $R^4$ represents 2,4-dichloro or 2-chloro-4-fluoro when n is 2. More particularly $R^4$ represents 2-chloro when n is 1 or $R^4$ represents 2,4-dichloro when n is 2.

Suitably n is 1, 2 or 3. Particularly n is 2 or 3.

"Pharmaceutically acceptable salt", where such salts are possible, includes both pharmaceutically acceptable acid and base addition salts. A suitable pharmaceutically acceptable salt of a compound of formula I is, for example, an acid-addition salt of a compound of formula I which is sufficiently basic, for example an acid-addition salt with an inorganic or organic acid for example a hydrochloride salt, a hydrosulphate salt, a sulphate salt, a methanesulphonate salt, a phenylsulphonate salt or a 1,5-naphthalene-disulphonate salt, or for example a salt of a compound of formula I which is sufficiently acidic with a base.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof and solvates thereof such as for instance hydrates. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention. All tautomers, where possible, are included within the scope of the invention. The present invention also encompasses compounds containing one or more isotopes for example $^{14}C$, $^{11}C$ or $^{19}F$ and their use as isotopically labelled compounds for pharmacological and metabolic studies.

The present invention also encompasses prodrugs of a compound of formula I that is compounds which are converted into a compound of formula I in vivo.

The following definitions shall apply throughout the specification and the appended claims.

Unless otherwise stated or indicated, the term "alkyl" denotes either a straight or branched alkyl group. Examples of said alkyl include methyl, ethyl, n-propyl, isopropyl, n-butyl, iso-butyl, sec-butyl or t-butyl. Preferred alkyl groups are methyl, ethyl, propyl, isopropyl, butyl and tertiary butyl.

Unless otherwise stated or indicated, the term "halogen" shall mean fluorine, chlorine, bromine or iodine.

Specific compounds of the invention include one or more of the following:

3,3,3-trifluoropropane-1-sulfonic acid 4-[1-(2-chlorophenyl)-3-methyl-4-oxo-5-piperidin-1-yl-4,5,6,7-tetrahydro-1H-pyrrolo[3,2-c]pyridine-2-yl]phenyl ester;

3,3,3-trifluoropropane-1-sulfonic acid 4-[1-(2,4-dichlorophenyl)-3-methyl-4-oxo-5-piperidin-1-yl-4,5,6,7-tetrahydro-1H-pyrrolo[3,2-c]pyridine-2-yl]phenyl ester;

3,3,3-trifluoropropane-1-sulfonic acid 4-[1-(2-chloro-4-fluorophenyl)-3-methyl-4-oxo-5-piperidin-1-yl-4,5,6,7-tetrahydro-1H-pyrrolo[3,2-c]pyridin-2-yl]phenyl ester;

1-(2-chlorophenyl)-3-methyl-5-piperidin-1-yl-2-[4-(4,4,4-trifluorobutoxy)phenyl] -1,5,6,7-tetrahydropyrrolo[3,2-c]pyridine-4-one;

3,3,3-trifluoropropane-1-sulfonic acid 4-[1-(2,4-dichlorophenyl)-3-methyl-4-oxo-5-piperidin-1-yl-4,5-dihydro-1H-pyrrolo[3,2-c]pyridin-2-yl]phenyl ester;

3,3,3-trifluoropropane-1-sulfonic acid 4-[1-(2-chloro-4-fluorophenyl)-3-methyl-4-oxo-5-piperidin-1-yl-4,5-dihydro-1H-pyrrolo[3,2-c]pyridin-2-yl]phenyl ester;

3,3,3-trifluoropropane-1-sulfonic acid 4-[1-(2-chlorophenyl)-5-(2-hydroxycyclohexyl)-3-methyl-4-oxo-4,5,6,7-tetrahydro-1H-pyrrolo[3,2-c]pyridin-2-yl]phenyl ester;

3,3,3-trifluoropropane-1-sulfonic acid 4-[1-(2,4-dichlorophenyl)-5-(2-hydroxycyclohexyl)-3-methyl-4-oxo-4,5,6,7-tetrahydro-1H-pyrrolo[3,2-c]pyridin-2-yl]phenyl ester;

3,3,3-trifluoropropane-1-sulfonic acid 4-[1-(2-chlorophenyl)-5-(3-hydroxycyclohexyl)-3-methyl-4-oxo-4,5,6,7-tetrahydro-1H-pyrrolo[3,2-c]pyridin-2-yl]phenyl ester;

3,3,3-trifluoropropane-1-sulfonic acid 4-[1-(2-chlorophenyl)-5-cyclohexyl-3-methyl-4-oxo-4,5,6,7-tetrahydro-1H-pyrrolo[3,2-c]pyridin-2-yl]phenyl ester;

3,3,3-trifluoropropane-1-sulfonic acid 4-[1-(2,4-dichlorophenyl)-5-(2-hydroxy-cyclohexyl)-3-methyl-4-oxo-4,5-dihydro-1H-pyrrolo[3,2-c]pyridin-2-yl]-phenyl ester;

3,3,3-trifluoropropane-1-sulfonic acid 4-[1-(2-chloro-phenyl)-5-cyclohexyl-3-hydroxymethyl-4-oxo-4,5,6,7-tetrahydro-1H-pyrrolo[3,2-c]pyridin-2-yl]phenyl ester;

3,3,3-trifluoropropane-1-sulfonic acid 4-[1-(2-chlorophenyl)-5-cyclohexyl-3-hydroxymethyl-4-oxo-4,5-dihydro-1H-pyrrolo[3,2-c]pyridin-2-yl]phenyl ester;

3,3,3-trifluoropropane-1-sulfonic acid 4-[1-(2-chlorophenyl)-5-(2-hydroxycyclohexyl)-3-hydroxymethyl-4-oxo-4,5-dihydro-1H-pyrrolo[3,2-c]pyridin-2-yl]phenyl ester;

3,3,3-trifluoro-propane- 1-sulfonic acid 4-(3-methyl-4-oxo-5-piperidin-1-yl-1-o-tolyl-4,5,6,7-tetrahydro-1H-pyrrolo[3,2-c]pyridin-2-yl)phenyl ester; and 1-(2,4-dichlorophenyl)-3-methyl-5-piperidin-1-yl-2-[4-(4,4,4-trifluoro-butoxy)phenyl]-1,5,6,7-tetrahydro-pyrrolo[3,2-c]pyridine-4-one;

as well as pharmaceutically acceptable salts thereof.

Methods of Preparation

Compounds of formula I in which $R^1$, $R^2$, $R^3$, n and $R^4$ are as previously defined may be prepared by reacting a compound of formula II

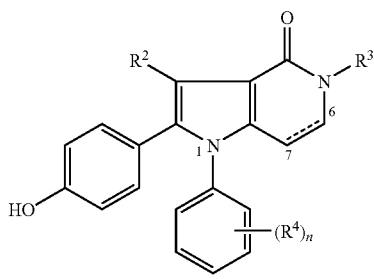

II in which $R^2$, $R^3$, $R^4$ and n are as previously defined with a compound of formula III $R^1X$  III in which $R^1$ is as previously defined and X represents a leaving group, for example chloro, bromo or iodo, in an inert solvent, for example dichloromethane or acetone, in the presence of a base, for example triethylamine, pyridine, 4-dimethylaminopyridine or potassium carbonate, at a temperature in the range of $-25°$ C. to $150°$ C.

Compounds of formula IA

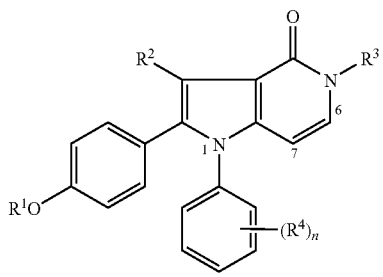

IA in which $R^1$, $R^2$, $R^3$, $R^4$ and n are as previously defined may be prepared by a) reacting a compound of formula IIB

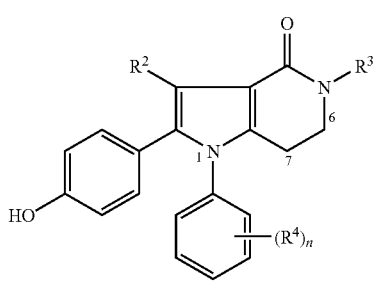

IIB in which $R^2$, $R^3$, $R^4$ and n are as previously defined with 2,3-dichloro-5,6-dicyano-1,4 benzoquinone (DDQ) in a solvent, for example 1,4-dioxane, at a temperature in the range of $0°$ C. to $60°$ C. to produce a compound of formula IIA

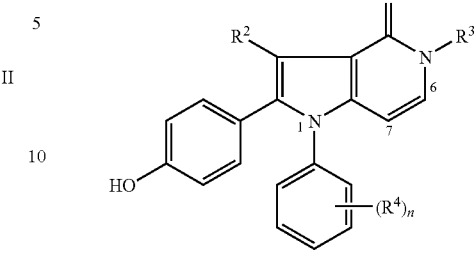

IIA in which $R^2$, $R^3$, $R^4$ and n are as previously defined and then b) reacting the compound of formula IIA with a compound of formula III $R^1X$  III in which $R^1$ is as previously defined and X represents a leaving group, for example chloro, bromo or iodo, in an inert solvent, for example dichloromethane or acetone, in the presence of a base, for example triethylamine, pyridine, 4-dimethylaminopyridine or potassium carbonate, at a temperature in the range of $-25°$ C. to $150°$ C.

Compounds of formula IA

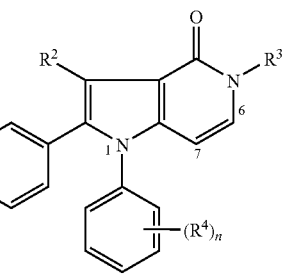

IA in which $R^1$, $R^2$, $R^3$, $R^4$ and n are as previously defined may also be prepared by reacting a compound of formula IB

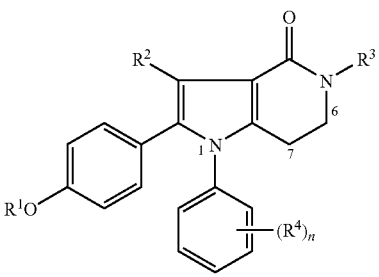

IB in which $R^1$, $R^2$, $R^3$, $R^4$ and n are as previously defined with bromine in a solvent, for example acetic acid or tetrahydrofuran or a mixture thereof, at a temperature in the range of $-80°$ C. to $50°$ C.

Certain compounds of formula II are believed to be novel and are herein claimed as part of the present invention.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable addition salt, in a pharmaceutically acceptable dosage form. Depending upon the disorder and patient to be treated and the route of administration, the compositions may be administered at varying doses.

Suitable daily doses of the compounds of the invention in the therapeutic treatment of humans are about 0.001-10 mg/kg body weight, preferably 0.01-1 mg/kg body weight. Oral formulations are preferred particularly tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

According to a further aspect of the invention there is also provided a pharmaceutical formulation including any of the compounds of the invention, or pharmaceutically acceptable derivatives thereof, in admixture with pharmaceutically acceptable adjuvants, diluents and/or carriers.

Pharmacological Properties

The compounds of formula (I) are useful for the treatment of obesity or being overweight, (e.g., promotion of weight loss and maintenance of weight loss), prevention of weight gain (e.g., medication-induced or subsequent to cessation of smoking), for modulation of appetite and/or satiety, eating disorders (e.g. binge eating, anorexia, bulimia and compulsive), cravings (for drugs, tobacco, alcohol, any appetizing macronutrients or non-essential food items), for the treatment of psychiatric disorders such as psychotic and/or mood disorders, schizophrenia and schizo-affective disorder, bipolar disorders, anxiety, anxio-depressive disorders, depression, mania, obsessive-compulsive disorders, impulse control disorders (e.g., Gilles de la Tourette's syndrome), attention disorders like ADD/ADHD, stress, and neurological disorders such as dementia and cognitive and/or memory dysfunction (e.g., amnesia, Alzheimer's disease, Pick's dementia, dementia of ageing, vascular dementia, mild cognitive impairment, age-related cognitive decline, and mild dementia of ageing), neurological and/or neurodegenerative disorders (e.g. Multiple Sclerosis, Raynaud's syndrome, Parkinson's disease, Huntington's chorea and Alzheimer's disease), demyelinisation-related disorders, neuroinflammatory disorders (e.g., Guillain-Barré syndrome).

The compounds are also potentially useful for the prevention or treatment of dependence and addictive disorders and behaviours (e.g., alcohol and/or drug abuse, pathological gambling, kleptomania), drug withdrawal disorders (e.g., alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances), alcohol and/or drug-induced mood, anxiety and/or sleep disorder with onset during withdrawal, and alcohol and/or drug relapse.

The compounds are also potentially useful for the prevention or treatment of neurological dysfunctions such as dystonias, dyskinesias, akathisia, tremor and spasticity, treatment of spinal cord injury, neuropathy, migraine, vigilance disorders, sleep disorders (e.g., disturbed sleep architecture, sleep apnea, obstructive sleep apnea, sleep apnea syndrome), pain disorders, cranial trauma.

The compounds are also potentially useful for the treatment of immune, cardiovascular disorders (e.g. atherosclerosis, arteriosclerosis, angina pectoris, abnormal heart rhythms, and arrhythmias, congestive heart failure, coronary artery disease, heart disease, hypertension, prevention and treatment of left ventricular hypertrophy, myocardial infarction, transient ischaemic attack, peripheral vascular disease, systemic inflammation of the vasculature, septic shock, stroke, cerebral apoplexy, cerebral infarction, cerebral ischaemia, cerebral thrombosis, cerebral embolism, cerebral hemorrhagia, metabolic disorders (e.g. conditions showing reduced metabolic activity or a decrease in resting energy expenditure as a percentage of total fat-free mass, diabetes mellitus, dyslipidemia, fatty liver, gout, hypercholesterolemia, hyperlipidemia, hypertriglyceridemia, hyperuricacidemia, impaired glucose tolerance, impaired fasting glucose, insulin resistance, insulin resistance syndrome, metabolic syndrome, syndrome X, obesity-hypoventilation syndrome (Pickwickian syndrome), type I diabetes, type II diabetes, low HDL- and/or high LDL-cholesterol levels, low adiponectin levels), reproductive and endocrine disorders (e.g. treatment of hypogonadism in males, treatment of infertility or as contraceptive, menstrual abnormalities/emmeniopathy, polycystic ovarian disease, sexual and reproductive dysfunction in women and men (erectile dysfunction), GH-deficient subjects, hirsutism in females, normal variant short stature) and diseases related to the respiratory (e.g. asthma and chronic obstructive pulmonary disease) and gastrointestinal systems (e.g. dysfunction of gastrointestinal motility or intestinal propulsion, diarrhea, emesis, nausea, gallbladder disease, cholelithiasis, obesity-related gastro-esophageal reflux, ulcers).

The compounds are also potentially useful as agents in treatment of dermatological disorders, cancers (e.g. colon, rectum, prostate, breast, ovary, endometrium, cervix, gallbladder, bile duct), craniopharyngioma, Prader-Willi syndrome, Turner syndrome, Frohlich's syndrome, glaucoma, infectious diseases, urinary tract disorders and inflammatory disorders (e.g. arthritis deformans, inflammation, inflammatory sequelae of viral encephalitis, osteoarthritis) and orthopedic disorders. The compounds are also potentially useful as agents in treatment of (esophageal) achalasia.

In another aspect the present invention provides a compound of formula I as previously defined for use as a medicament.

In a further aspect the present invention provides the use of a compound of formula I in the preparation of a medicament for the treatment or prophylaxis of obesity or being overweight, (e.g., promotion of weight loss and maintenance of weight loss), prevention of weight gain (e.g., medication-induced or subsequent to cessation of smoking), for modulation of appetite and/or satiety, eating disorders (e.g. binge eating, anorexia, bulimia and compulsive), cravings (for drugs, tobacco, alcohol, any appetizing macronutrients or non-essential food items), for the treatment of psychiatric disorders such as psychotic and/or mood disorders, schizophrenia and schizo-affective disorder, bipolar disorders, anxiety, anxio-depressive disorders, depression, mania, obsessive-compulsive disorders, impulse control disorders (e.g., Gilles de la Tourette's syndrome), attention disorders like ADD/ADHD, stress, and neurological disorders such as dementia and cognitive and/or memory dysfunction (e.g., amnesia, Alzheimer's disease, Pick's dementia, dementia of ageing, vascular dementia, mild cognitive impairment, age-related cognitive decline, and mild dementia of ageing), neurological and/or neurodegenerative disorders (e.g. Multiple Sclerosis, Raynaud's syndrome, Parkinson's disease, Huntington's chorea and Alzheimer's disease), demyelinisation-related disorders, neuroinflammatory disorders (e.g., Guillain-Barré syndrome).

In a further aspect the present invention provides the use of a compound of formula I in the preparation of a medicament for the treatment or prophylaxis of dependence and addictive disorders and behaviours (e.g., alcohol and/or drug abuse, pathological gambling, kleptomania), drug withdrawal disorders (e.g., alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances), alcohol and/or drug-induced mood, anxiety and/or sleep disorder with onset during withdrawal, and alcohol and/or drug relapse.

In a further aspect the present invention provides the use of a compound of formula I in the preparation of a medicament for the treatment or prophylaxis of neurological dysfunctions such as dystonias, dyskinesias, akathisia, tremor and spasticity, treatment of spinal cord injury, neuropathy, migraine, vigilance disorders, sleep disorders (e.g., disturbed sleep architecture, sleep apnea, obstructive sleep apnea, sleep apnea syndrome), pain disorders, cranial trauma.

In a further aspect the present invention provides the use of a compound of formula I in the preparation of a medicament for the treatment or prophylaxis of immune, cardiovascular disorders (e.g. atherosclerosis, arteriosclerosis, angina pectoris, abnormal heart rhythms, and arrhythmias, congestive heart failure, coronary artery disease, heart disease, hypertension, prevention and treatment of left ventricular hypertrophy, myocardial infarction, transient ischaemic attack, peripheral vascular disease, systemic inflammation of the vasculature, septic shock, stroke, cerebral apoplexy, cerebral infarction, cerebral ischaemia, cerebral thrombosis, cerebral embolism, cerebral hemorrhagia, metabolic disorders (e.g. conditions showing reduced metabolic activity or a decrease in resting energy expenditure as a percentage of total fat-free mass, diabetes mellitus, dyslipidemia, fatty liver, gout, hypercholesterolemia, hyperlipidemia, hypertriglyceridemia, hyperuricacidemia, impaired glucose tolerance, impaired fasting glucose, insulin resistance, insulin resistance syndrome, metabolic syndrome, syndrome X, obesity-hypoventilation syndrome (Pickwickian syndrome), type I diabetes, type II diabetes, low HDL- and/or high LDL-cholesterol levels, low adiponectin levels), reproductive and endocrine disorders (e.g. treatment of hypogonadism in males, treatment of infertility or as contraceptive, menstrual abnormalities/emmeniopathy, polycystic ovarian disease, sexual and reproductive dysfunction in women and men (erectile dysfunction), GH-deficient subjects, hirsutism in females, normal variant short stature) and diseases related to the respiratory (e.g. asthma and chronic obstructive pulmonary disease) and gastrointestinal systems (e.g. dysfunction of gastrointestinal motility or intestinal propulsion, diarrhea, emesis, nausea, gallbladder disease, cholelithiasis, obesity-related gastro-esophageal reflux, ulcers).

In a further aspect the present invention provides the use of a compound of formula I in the preparation of a medicament for the treatment or prophylaxis of dermatological disorders, cancers (e.g. colon, rectum, prostate, breast, ovary, endometrium, cervix, gallbladder, bile duct), craniopharyngioma, Prader-Willi syndrome, Turner syndrome, Frohlich's syndrome, glaucoma, infectious diseases, urinary tract disorders and inflammatory disoerders (e.g. arthritis deformans, inflammation, inflammatory sequelae of viral encephalitis, osteoarthritis) and orthopedic disorders.

In a still further aspect the present invention provides a method comprising administering a pharmacologically effective amount of a compound of formula I to a patient in need thereof for the prophylaxis or treatment of obesity or being overweight, (e.g., promotion of weight loss and maintenance of weight loss), prevention of weight gain (e.g., medication-induced or subsequent to cessation of smoking), for modulation of appetite and/or satiety, eating disorders (e.g. binge eating, anorexia, bulimia and compulsive), cravings (for drugs, tobacco, alcohol, any appetizing macronutrients or non-essential food items), for the treatment of psychiatric disorders such as psychotic and/or mood disorders, schizophrenia and schizo-affective disorder, bipolar disorders, anxiety, anxio-depressive disorders, depression, mania, obsessive-compulsive disorders, impulse control disorders (e.g., Gilles de la Tourette's syndrome), attention disorders like ADD/ADHD, stress, and neurological disorders such as dementia and cognitive and/or memory dysfunction (e.g., amnesia, Alzheimer's disease, Pick's dementia, dementia of ageing, vascular dementia, mild cognitive impairment, age-related cognitive decline, and mild dementia of ageing), neurological and/or neurodegenerative disorders (e.g. Multiple Sclerosis, Raynaud's syndrome, Parkinson's disease, Huntington's chorea and Alzheimer's disease), demyelinisation-related disorders, neuroinflammatory disorders (e.g., Guillain-Barré syndrome).

In a still further aspect the present invention provides a method comprising administering a pharmacologically effective amount of a compound of formula I to a patient in need thereof for the prophylaxis or treatment of dependence and addictive disorders and behaviours (e.g., alcohol and/or drug abuse, pathological gambling, kleptomania), drug withdrawal disorders (e.g., alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances), alcohol and/or drug-induced mood, anxiety and/or sleep disorder with onset during withdrawal, and alcohol and/or drug relapse.

In a still further aspect the present invention provides a method comprising administering a pharmacologically effective amount of a compound of formula I to a patient in need thereof for the prophylaxis or treatment of neurological dysfunctions such as dystonias, dyskinesias, akathisia, tremor and spasticity, treatment of spinal cord injury, neuropathy, migraine, vigilance disorders, sleep disorders (e.g., disturbed sleep architecture, sleep apnea, obstructive sleep apnea, sleep apnea syndrome), pain disorders, cranial trauma.

In a still further aspect the present invention provides a method comprising administering a pharmacologically effective amount of a compound of formula I to a patient in need thereof for the prophylaxis or treatment of immune, cardiovascular disorders (e.g. atherosclerosis, arteriosclerosis, angina pectoris, abnormal heart rhythms, and arrhythmias, congestive heart failure, coronary artery disease, heart disease, hypertension, prevention and treatment of left ventricular hypertrophy, myocardial infarction, transient ischaemic attack, peripheral vascular disease, systemic inflammation of the vasculature, septic shock, stroke, cerebral apoplexy, cerebral infarction, cerebral ischaemia, cerebral thrombosis, cerebral embolism, cerebral hemorrhagia, metabolic disorders (e.g. conditions showing reduced metabolic activity or a decrease in resting energy expenditure as a percentage of total fat-free mass, diabetes mellitus, dyslipidemia, fatty liver, gout, hypercholesterolemia, hyperlipidemia, hypertriglyceridemia, hyperuricacidemia, impaired glucose tolerance, impaired fasting glucose, insulin resistance, insulin resistance syndrome, metabolic syndrome, syndrome X, obesity-hypoventilation syndrome (Pickwickian syndrome), type I diabetes, type II diabetes, low HDL- and/or high LDL-cholesterol levels, low adiponectin levels), reproductive and endocrine disorders (e.g. treatment of hypogonadism in males, treatment of infertility or as contraceptive, menstrual abnormalities/emmeniopathy, polycystic ovarian disease, sexual and reproductive dysfunction in women and men (erectile dysfunction), GH-deficient subjects, hirsutism in females, normal variant short stature) and diseases related to the respiratory (e.g. asthma and chronic obstructive pulmonary disease) and gastrointestinal systems (e.g. dysfunction of gastrointestinal motility or intestinal propulsion, diarrhea, emesis, nausea, gallbladder disease, cholelithiasis, obesity-related gastro-esophageal reflux, ulcers).

In a still further aspect the present invention provides a method comprising administering a pharmacologically effective amount of a compound of formula I to a patient in need thereof for the prophylaxis or treatment of dermatological disorders, cancers (e.g. colon, rectum, prostate, breast, ovary, endometrium, cervix, gallbladder, bile duct), craniopharyngioma, Prader-Willi syndrome, Turner syndrome, Frohlich's syndrome, glaucoma, infectious diseases, urinary tract disorders and inflammatory disorders (e.g. arthritis deformans, inflammation, inflammatory sequelae of viral encephalitis, osteoarthritis) and orthopedic disorders.

The compounds of the present invention are particulary suitable for the treatment of obesity or being overweight, (e.g., promotion of weight loss and maintenance of weight loss), prevention or reversal of weight gain (e.g., rebound, medication-induced or subsequent to cessation of smoking), for modulation of appetite and/or satiety, eating disorders (e.g. binge eating, anorexia, bulimia and compulsive), cravings (for drugs, tobacco, alcohol, any appetizing macronutrients or non-essential food items).

The compounds of formula (I) are useful for the treatment of obesity, psychiatric disorders such as psychotic disorders, schizophrenia, bipolar disorders, anxiety, anxio-depressive disorders, depression, cognitive disorders, memory disorders, obsessive-compulsive disorders, anorexia, bulimia, attention disorders like ADHD, epilepsy, and related conditions, and neurological disorders such as dementia, neurological disorders(e.g. Multiple Sclerosis), Raynaud's syndrome, Parkinson's disease, Huntington's chorea and Alzheimer's disease. The compounds are also potentially useful for the treatment of immune, cardiovascular, reproductive and endocrine disorders, septic shock and diseases related to the respiratory and gastrointestinal systems (e.g. diarrhea). The compounds are also potentially useful as agents in treatment of extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms. The compounds may also eliminate the increase in weight that normally accompanies the cessation of smoking.

In another aspect the present invention provides a compound of formula I as previously defined for use as a medicament.

In a further aspect the present invention provides the use of a compound of formula I in the preparation of a medicament for the treatment or prophylaxis of obesity, psychiatric disorders such as psychotic disorders, schizophrenia, bipolar disorders, anxiety, anxio-depressive disorders, depression, cognitive disorders, memory disorders, obsessive-compulsive disorders, anorexia, bulimia, attention disorders like ADHD, epilepsy, and related conditions, neurological disorders such as dementia, neurological disorders (e.g. Multiple Sclerosis), Parkinson's Disease, Huntington's Chorea and Alzheimer's Disease, immune, cardiovascular, reproductive and endocrine disorders, septic shock, diseases related to the respiratory and gastrointestinal systems (e.g. diarrhea), and extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms.

In a still further aspect the present invention provides a method of treating obesity, psychiatric disorders such as psychotic disorders such as schizophrenia and bipolar disorders, anxiety, anxio-depressive disorders, depression, cognitive disorders, memory disorders, obsessive-compulsive disorders, anorexia, bulimia, attention disorders like ADHD, epilepsy, and related conditions, neurological disorders such as dementia, neurological disorders (e.g. Multiple Sclerosis), Parkinson's Disease, Huntington's Chorea and Alzheimer's Disease, immune, cardiovascular, reproductive and endocrine disorders, septic shock, diseases related to the respiratory and gastrointestinal systems (e.g. diarrhea), and extended abuse, addiction and/or relapse indications, e.g. treating drug (nicotine, is ethanol, cocaine, opiates, etc) dependence and/or treating drug (nicotine, ethanol, cocaine, opiates, etc) withdrawal symptoms comprising administering a pharmacologically effective amount of a compound of formula I to a patient in need thereof.

The compounds of the present invention are particulary suitable for the treatment of obesity, e.g. by reduction of appetite and body weight, maintenance of weight reduction and prevention of rebound.

The compounds of the present invention may also be used to prevent or reverse medication-induced weight gain, e.g. weight gain caused by antipsychotic (neuroleptic) treatment(s). The compounds of the present invention may also be used to prevent or reverse weight gain associated with smoking cessation.

The compounds of the present invention are suitable for use in treating the above indications in juvenile or adolescent patient populations.

The compounds of the present invention may also be suitable for use in the regulation of bone mass and bone loss and therefore useful in the treatment of osteoporosis and other bone diseases.

The compounds of the present invention may also be used in the treatment of hepatic diseases, for example hepatic fibrosis, alcoholic liver cirrhosis, chronic viral hepatitis, non-alcoholic steato or liver cancerhepatitis Combination Therapy The compounds of the invention may be combined with another therapeutic agent that is useful in the treatment of obesity such as other anti-obesity drugs, that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or G-I motility.

The compounds of the invention may further be combined with another therapeutic agent that is useful in the treatment of disorders associated with obesity such as hypertension, hyperlipidaemias, dyslipidaemias, diabetes, sleep apnea, asthma, heart disorders, atherosclerosis, macro and micro vascular diseases, liver steatosis, cancer, joint disorders, and gallbladder disorders. For example, a compound of the present invention may be used in combination with a another therapeutic agent that lowers blood pressure or that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of obesity and its associated complications the metabolic syndrome and type 2 diabetes, these include biguanide drugs, insulin (synthetic insulin analogues) and oral antihyperglycemics (these are divided into prandial glucose regulators and alpha-glucosidase inhibitors).

In another aspect of the invention, the compound of formula I, or a pharmaceutically acceptable salt thereof may be administered in association with a PPAR modulating agent. PPAR modulating agents include but are not limited to a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art.

In addition the combination of the invention may be used in conjunction with a sulfonylurea. The present invention also includes a compound of the present invention in combination with a cholesterol-lowering agent. The cholesterol-lowering agents referred to 30 in this application include but are not limited to inhibitors of HMG-CoA reductase (3-hydroxy-3-methylglutaryl coenzyme A reductase). Suitably the HMG-CoA reductase inhibitor is a statin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with an inhibitor of the ileal bile acid transport system (IBAT inhibitor). The present invention also includes a compound of the present invention in combination with a bile acid binding resin.

The present invention also includes a compound of the present invention in combination with a bile acid sequestering agent, for example colestipol or cholestyramine or cholestagel.

According to an additional further aspect of the present invention there is provided a combination treatment comprising the administration of an effective amount of a compound of the formula I, or a pharmaceutically acceptable salt thereof, optionally together with a pharmaceutically acceptable diluent or carrier, with the simultaneous, sequential or separate administration one or more of the following agents selected from:

a CETP (cholesteryl ester transfer protein) inhibitor;
a cholesterol absorption antagonist;
a MTP (microsomal transfer protein) inhibitor;
a nicotinic acid derivative, including slow release and combination products;
a phytosterol compound;
probucol;
an anti-coagulant;
an omega-3 fatty acid;
another anti-obesity compound for example sibutramine, phentermine, orlistat, bupropion, ephedrine, thyroxine;
an antihypertensive compound for example an angiotensin converting enzyme (ACE) inhibitor, an angiotensin II receptor antagonist, an adrenergic blocker, an alpha adrenergic blocker, a beta adrenergic blocker, a mixed alpha/beta adrenergic blocker, an adrenergic stimulant, calcium channel blocker, an AT-1 blocker, a saluretic, a diuretic or a vasodilator;
a melanin concentrating hormone (MCH) modulator;
an NPY receptor modulator;
an orexin receptor modulator;
a phosphoinositide-dependent protein kinase (PDK) modulator; or
modulators of nuclear receptors for example LXR, FXR, RXR, GR, ERR$\alpha$, $\beta$, PPAR$\alpha$, $\beta$, $\gamma$ and ROR alpha;
a monoamine transmission-modulating agent, for example a selective serotonin reuptake inhibitor (SSRI), a noradrenaline reuptake inhibitor (NARI), a noradrenaline-serotonin reuptake inhibitor (SNRI), a monoamine oxidase inhibitor (MAOI), a tricyclic antidepressive agent (TCA), a noradrenergic and specific serotonergic antidepressant (NaSSA);
an antipsychotic agent for example olanzapine and clozapine;
a serotonin receptor modulator;
a leptin/leptin receptor modulator;
a ghrelin/ghrelin receptor modulator;
a DPP-IV inhibitor;
or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula I, or a pharmaceutically acceptable salt thereof, optionally together with a pharmaceutically acceptable diluent or carrier, with the simultaneous, sequential or separate administration of very low calorie diets (VLCD) or low-calorie diets (LCD).

Therefore in an additional feature of the invention, there is provided a method for the treatment of obesity and its associated complications in a warm-blooded animal, such as man, in need of such treatment which comprises administering to said animal an effective amount of a compound of formula I, or a pharmaceutically acceptable salt thereof in simultaneous, sequential or separate administration with an effective amount of a compound from one of the other classes of compounds described in this combination section, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula I, or a pharmaceutically acceptable salt thereof in simultaneous, sequential or separate administration with an effective amount of a compound from one of the other classes of compounds described in this combination section or a pharmaceutically acceptable salt, solvate, solvate of such a salt or a prodrug thereof.

According to a further aspect of the invention there is provided a pharmaceutical composition which comprises a compound of formula I, or a pharmaceutically acceptable salt thereof, and a compound from one of the other classes of compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula I, or a pharmaceutically acceptable salt thereof, and a compound from one of the other classes of compounds described in this combination section or a pharmaceutically acceptable salt, solvate, solvate of such a salt or a prodrug thereof.

According to a further aspect of the present invention there is provided a kit comprising:
a) a compound of formula I, or a pharmaceutically acceptable salt thereof, in a first unit dosage form;
b) a compound from one of the other classes of compounds described in this combination section or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula I, or a pharmaceutically acceptable salt thereof, together with a pharmaceutically acceptable diluent or carrier, in a first unit dosage form;
b) a compound from one of the other classes of compounds described in this combination section or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula I, or a pharmaceutically acceptable salt thereof, and one of the other compounds described in this combination section, or a pharmaceutically acceptable salt, solvate, solvate of such a salt or a prodrug thereof, in the manufacture of a medicament for use in the treatment of obesity and its associated complications in a warm-blooded animal, such as man.

According to another feature of the invention there is provided the use of a compound of the formula I, or a pharmaceutically acceptable salt thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula I, or a pharmaceutically acceptable salt thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Furthermore, a compound of the invention may also be combined with therapeutic agents that are useful in the treatment of disorders or conditions associated with obesity (such as type II diabetes, metabolic syndrome, dyslipidemia, impaired glucose tolerance, hypertension, coronary heart disease, non-alcoholic steatohepatitis, osteoarthritis and some cancers) and psychiatric and neurological conditions.

It will be understood that there are medically accepted definitions of obesity and being overweight. A patient may be identified by, for example, measuring body mass index (BMI), which is calculated by dividing weight in kilograms by height in metres squared, and comparing the result with the definitions.

As the compounds of formula I are useful in causing smoking cessation, preventing weight gain resulting from smoking cessation, treating nicotine withdrawal and preventing nicotine dependence they may also be combined with other compounds known to have one or more of these effects for example nicotine, a nicotine agonist or a partial agonist, a monoamine oxidase inhibitor or antidepressants such as bupropion, doxepine, nortriptyline or an anxiolytic such as buspirone or clonidine.

Pharmacological Activity

Compounds of the present invention are active against the receptor product of the CB1 gene. The affinity of the compounds of the invention for central cannabinoid receptors is demonstrable in methods described in Devane et al , Molecular Pharmacology, 1988, 34,605 or those described in WO01/70700 or EP 656354. Alternatively the assay may be performed as follows.

10 µg of membranes prepared from cells stably transfected with the CB1 gene were suspended in 200 µl of 100 mM NaCl, 5 mM $MgCl_2$, 1 mM EDTA, 50 mM HEPES (pH 7.4), 1 mM DTT, 0.1% BSA and 100 µM GDP. To this was added an EC80 concentration of agonist (CP55940), the required concentration of test compound and 0.1 µCi [$^{35}$S]-GTPγS. The reaction was allowed to proceed at 30° C. for 45 min. Samples were then transferred on to GF/B filters using a cell harvester and washed with wash buffer (50 mM Tris (pH 7.4), 5mM $MgCl_2$, 50 mM NaCl). Filters were then covered with scintilant and counted for the amount of [$^{35}$S]-GTPγS retained by the filter.

Activity is measured in the absence of all ligands (minimum activity) or in the presence of an EC80 concentration of CP55940 (maximum activity). These activities are set as 0% and 100% activity respectively. At various concentrations of novel ligand, activity is calculated as a percentage of the maximum activity and plotted. The data are fitted using the equation $y=A+((B-A)/1+((C/x) \text{ UD}))$ and the IC50 value determined as the concentration required to give half maximal inhibition of GTPγS binding under the conditions used.

The compounds of the present invention are active at the CB1 receptor (IC50<1 micromolar). Most preferred compounds have IC50<200 nanomolar. For example, Example 1 has an IC50 of 0.98 nM.

The compounds of the invention are believed to be selective CB1 antagonists or inverse agonists. The potency, selectivity profile and side effect propensity may limit the clinical usefulness of hitherto known compounds with alleged CB1 antagonistic/inverse agonistic properties. In this regard, preclinical evaluation of compounds of the present invention in models of gastrointestinal and/or cardiovascular function indicates that they offer significant advantages compared to representative reference CB1 antagonist/inverse agonist agents.

The compounds of the present invention may provide additional benefits in terms of potency, selectivity profile, bioavailability, half-life in plasma, blood brain permeability, plasma protein binding (for example higher free fraction of drug) or solubility compared to representative reference CB1 antagonists/inverse agonist agents.

The compounds of the present invention have improved solubility in organic solvents compared to compounds in the prior art. For example, Example 19 of WO03/027114 (2-(4-chlorophenyl)-1-(2,4-dichlorophenyl)-3-methyl-5-(1-piperidinyl)-1,5,6,7-tetrahydro-4H-pyrrolo-[3,2-c]pyridin-4-one) was found to be insoluble in dimethyl sulfoxide whereas the compounds of the present invention were all soluble in dimethyl sulfoxide. It would be expected that this increase in solubility in organic solvents would lead to improvements in bioavailability and ease of manufacture and formulation.

The utility of the compounds of the present invention in the treatment of obesity and related conditions is demonstrated by a decrease in body weight in cafeteria diet-induced obese mice. Female C57B1/6J mice were given ad libitum access to calorie-dense 'cafeteria' diet (soft chocolate/cocoa-type pastry, chocolate, fatty cheese and nougat) and standard lab chow for 8-10 weeks. Compounds to be tested were then administered systemically (iv, ip, sc or po) once daily for a minimum of 5 days, and the body weights of the mice monitored on a daily basis. Simultaneous assessment of adiposity was carried by means of DEXA imaging at baseline and termination of the study. Blood sampling was also carried out to assay changes in obesity-related plasma markers. Compounds of the present invention show superior weight reduction compared to prior art compounds.

EXAMPLES

Abbreviations
DDQ 2,3-dichloro-5,6-dicyano-1,4-benzoquinone
DME dimethoxyethane
DMF dimethylformamide
EtOAc ethyl acetate
NBS N-bromosuccinimide
MeOH methanol
p-TSA toluenesulphonic acid
rt room temperature
TBAF tetrabutylammonium fluoride
TEA triethylamine
TFA trifluoroacetic acid
THF tetrahydrofuran
t triplet
s singlet
d doublet
q quartet
qvint quintet
m multiplet
br broad
bs broad singlet
dm doublet of multiplet
bt broad triplet
dd doublet of doublet General Experimental Procedures Mass spectra were recorded on either a Micromass ZQ single quadrupole or a Micromass LCZ single quadrupole mass spectrometer both equipped with a pneumatically assisted electrospray interface (LC-MS). $^1$H NMR measurements were performed on either a Varian Mercury 300 or a Varian Inova 500, operating at $^1$H frequencies of 300 and 500 MHz respectively. Chemical shifts are given in ppm with CDCl$_3$ as internal standard. CDCl$_3$ is used as the solvent for NMR unless otherwise stated. Purification was performed on a semipreparative HPLC (High Performance Liquid Chromatography) with a mass triggered fraction collector, Shimadzu QP 8000 single quadrupole mass spectrometer equipped with 19×100 mm C8 column. The mobile phase used was, if nothing else is stated, acetonitrile and buffer (0.1 M ammonium acetate:acetonitrile 95:5).

Example 1

3,3,3-Trifluoropropane-1-sulfonic acid 4-[1-(2-chlorophenyl)-3-methyl-4-oxo-5-piperidin-1-yl-4,5,6,7-tetrahydro-1H-pyrrolo[3,2-c]pyridine-2-yl]phenyl ester Step 1 3-(Piperidin-1-ylamino)propionic acid methyl ester To a solution of 1-aminopiperidine (100 g, 1.00 mol) in dry methanol at 0° C., methyl acrylate (99.0 ml, 1.10 mol) was added dropwise. The resulting mixture was stirred at room temperature overnight. After evaporation of the solvent, heptane was added to the residue, and the white solid (impurity) removed by filtration. The filtrate was concentrated to dryness to afford 80.0 g (43%) of the title compound as a yellow oil.

Step 2 N-(2-Methoxycarbonylethyl)-N-piperidin-1-yl-maloamic acid ethyl ester

To a solution of 3-(piperidin-1-ylamino)propionic acid methyl ester (80.0 g, 0.43 mol) in dichloromethane was added triethylamine (71.0 ml, 0.50 mol) followed by slow addition of ethyl malonyl chloride (60.0 ml, 0.47 mol) at 0° C. The resulting slurry was stirred at room temperature for 4 hours. Water was added and the phases separated. The organic phase was dried (Na$_2$SO$_4$), filtered and concentrated. Flash chromatography (toluene: EtOAc 9:1-1:1) gave 81.0 g (63%) of the product as an oil used without further purification.

Step 3 2,4-Dioxo-[1,1']bipiperidinyl-3-carboxylic acid ethyl ester

To a solution of N-(2-methoxycarbonylethyl)-N-piperidin-1-yl-maloamic acid ethyl ester (60.0 g, 0.20 mol) in a mixture of THF (1100 ml) and DMF (490 ml) was added cesium carbonate (195 g, 0.60 mol). The resulting mixture was boiled under reflux (80° C.) for 48 hours. The cooled reaction mixture was filtered and the filtrate evaporated. The combined is filtered solid and the filtrate residue were purified by flash chromatography (CH$_2$Cl$_2$:MeOH 70:30) to give 15.0 g (28%) of the title compound as a pale yellow oil.

Step 4 [1,1']Bipiperidinyl-2,4-dione

The oil from step 3 was dissolved in 10% acetic acid (250 ml) and the solution boiled under reflux for one hour. The cooled reaction mixture was evaporated, and the residue purified by flash chromatography (CH$_2$Cl$_2$: acetone 9:1-1:1) to give 4.00 g (36%) of the title compound as a semi-solid.

Step 5 1-(2-Chlorophenylamino)-propan-2-one

A mixture of 2-chloroaniline (13.2 ml, 0.125 mol), iodoacetone (26.6 g, 0.145 mol) and potassium carbonate (18.1 g, 0.13 mol) in DMF (200 ml) was heated under nitrogen at 100° C. overnight. After cooling to rt, water was added and the mixture extracted with ether (×3). The combined organic extracts were washed with water, dried (Na$_2$SO$_4$), filtered and concentrated. Flash chromatography (Heptane:EtOAc 80:20) afforded 16.0 g (70%) of the title compound as a brown liquid.

Step 6 1-(2-Chlorophenyl)-3-methyl-5-piperidin-1-yl-1,5,6,7-tetrahydropyrrolo[3,2-c]pyridine-4-one To a solution of [1,1']bipiperidinyl-2,4-dione, from Step 4 (2.49 g, 12.7 mmol) in dry toluene (240 ml) at room temperature were added 1-(2-chlorophenylamino)propan-2-one (2.33 mg, 12.7 mmol) from Step 5 followed by a catalytic amount of p-TSA. The reaction mixture was boiled under reflux with a Dean-Stark trap, and 90 ml toluene was collected in the trap. Then 1 molar equivalent of p-TSA was added and the reaction mixture was boiled under reflux overnight. After cooling to room temperature, the reaction mixture was evaporated and purified by flash chromatography (heptane: EtOAc gradient) to give 0.93 g (21%) of the title compound.

Step 7 2-Bromo-1-(2-chlorophenyl)-3-methyl-5-piperidin-1-yl-1,5,6,7-tetrahydropyrrolo[3,2-c]pyridine-4-one To as solution of 1-(2-chlorophenyl)-3-methyl-5-piperidin-1-yl-1,5,6,7-tetrahydro-pyrrolo[3,2-c]pyridine-4-one (0.93 g, 2.70 mmol) in DMF (30 ml) was added NBS (0.50, 2.84 mmol) at 0° C. The reaction mixture was stirred at this temperature for one hour and then water was added. The mixture was extracted with ether (×3). The combined ether extracts were dried ($Na_2SO_4$), filtered and concentrated to give 0.92 g (84%) of the title compound after flash chromatography (heptane:EtOAc gradient).

Step 8 1-(2-Chlorophenyl)-2-(4-hydroxyphenyl)-3-methyl-5-piperidin-1-yl-1,5,6,7-tetrahydro-pyrrolo[3,2-c]pyridine-4-one 2-Bromo-1-(2-chlorophenyl)-3-methyl-5-piperidin-1-yl-1,5,6,7-tetrahydro-pyrrolo[3,2-c]pyridine-4-one (0.92 g, 2.25 mmol), 4-hydroxyphenylboronic acid (0.35 g, 2.50 mmol) and tetrakis(triphenylphosphine)palladium(0) (350 mg) were dissolved in DME (46 ml) and 1 M $Na_2CO_3$ (12 ml)). The resulting solution was degassed and heated at 60° C. under nitrogen overnight. Water and EtOAc were added after cooling and the aqueous phase extracted with EtOAc (×3). The combined organic extracts were dried ($Na_2SO_4$), filtered and concentrated to give a crude product that was purified by flash chromatography (heptane:EtOAc gradient) to afford 0.54 g (55%) of the product as a pale yellow solid.

Step 9 3,3,3-Trifluoropropane-1-sulfonic acid 4-[1-(2-chlorophenyl)-3-methyl-4-oxo-5-piperidin-1-yl-4,5,6,7-tetrahydro-1H-pyrrolo[3,2-c]pyridine-2-yl]phenyl ester To a solution of 1-(2-chlorophenyl)-2-(4-hydroxyphenyl)-3-methyl-5-piperidin-1-yl-1,5,6,7-tetrahydropyrrolo[3,2-c] pyridine-4-one (0.54 g, 1.24 mmol) in dichloromethane (30 ml) at 0° C. was added triethylamine (0.20 ml, 1.50 mmol) followed by 3,3,3-30 trifluoropropane sulfonyl chloride (295 mg, 1.50 mmol). The reaction mixture was subsequently stirred at room temperature for 2.5 hours. Concentration and purification by flash chromatography (heptane:EtOAc gradient) afforded 65 mg (9%) of the title compound as a colorless solid.

$^1$H NMR ($CDCl_3$): δ 7.57-7.08 (8H, m), 3.78-3.71 (2H, m), 3.50-3.44 (2H, m), 3.40-3.00 (2H, broad s), 2.85-2.65 (4H, m), 2.41 (3H, s), 1.80-1.50 (6H, m), 1.40-1.20 (2H, m). MS: 596 (M+H). HPLC: 93%

Example 2

3,3,3-Trifluoropropane-1-sulfonic acid 4-[1-(2,4-dichlorophenyl)-3-methyl-4-oxo-5-piperidin-1-yl-4,5,6,7-tetrahydro-1H-pyrrolo[3,2-c]pyridine-2-yl] phenyl ester Step 1 1-(2,4-Dichlorophenylamino)propan-2-one A mixture of 2,4-dichloroaniline (20.2 g, 0.125 mol), iodoacetone (26.6 g, 0.145 mol) and potassium carbonate (18.1 g, 0.13 mol) in DMF (200 ml) was heated under nitrogen at 100° C. overnight. After cooling to rt, water was added and the mixture extracted with ether (×3). The combined organic extracts were washed with water, dried ($Na_2SO_4$), filtered and concentrated. Flash chromatography (Heptane: EtOAc 90:10-80:20) afforded 13.6 g (50%) of the title compound as a brown solid.

Step 2 1-(2,4-Dichlorophenyl)-3-methyl-5-piperidin-1-yl-1,5,6,7-tetrahydro-pyrrolo[3,2-c]pyridine-4-one To a solution of [1,1']bipiperidinyl-2,4-dione (520 mg, 2.65 mmol) from Example 1 step 4 in dry toluene (25 ml) at room temperature were added 1-(2,4-dichlorophenylamino)-propan-2-one (576 mg, 2.64 mmol) from Step 1 above followed by a catalytic amount of p-TSA. The reaction mixture was boiled under reflux with a Dean-Stark trap, and 10 ml toluene was collected in the trap. One molar equivalent of p-TSA (250 mg) was added and the reaction mixture was boiled under reflux for 5.5 hours. After cooling to room temperature, the reaction mixture was evaporated and purified by flash chromatography (heptane:EtOAc gradient) to give 250 mg (25%) of the title compound as a brown solid. A parallel experiment with 1.51 g 1-(2,4-dichlorophenylamino)propan-2-one afforded 0.68 g (26%) of the product.

Step 3 2-Bromo-1-(2,4-dichlorophenyl)-3-methyl-5-piperidin-1-yl-1,5,6,7-tetrahydro-pyrrolo[3,2-c]pyridine-4-one To as solution of 1-(2,4-dichlorophenyl)-3-methyl-5-piperidin-1-yl-1,5,6,7-tetrahydropyrrolo[3,2-c]pyridine-4-one (0.93 g, 2.46 mmol) in DMF (25 ml) was added NBS (0.48, 2.71 mmol) at 0° C. The reaction mixture was stirred at this temperature for one hour and then water was added. The mixture was extracted with ether (×3). The combined ether extracts were dried ($Na_2SO_4$), filtered and concentrated to give 0.45 g (40%) of the title compound after flash chromatography (heptane:EtOAc gradient).

Step 4 1-(2,4-Dichlorophenyl)-2-(4-hydroxyphenyl)-3-methyl-5-piperidin-1-yl-1,5,6,7-tetrahydro-pyrrolo[3,2-c]pyridine-4-one 2-Bromo-1-(2,4-Dichlorophenyl)-3-methyl-5-piperidin-1-yl-1,5,6,7-tetrahydropyrrolo[3,2-c]pyridine-4-one (450 mg, 0.98 mmol), 4-hydroxyphenylboronic acid (150 mg, 1.09 mmol) and tetrakis(triphenylphosphine)palladium(0) (150 mg) were dissolved in DME (20 ml) and 1 M $Na_2CO_3$ (5 ml)). The resulting solution was degassed and heated at 60° C. under nitrogen overnight. Water and EtOAc were added after cooling and the aqueous phase extracted with EtOAc (×3). The combined organic extracts were dried ($Na_2SO_4$), filtered and concentrated to give a crude product that was purified by flash chromatography (heptane:EtOAc gradient) to afford 0.40 g (87%) of the product as a pale yellow solid.

Step 5 3,3,3-Trifluoropropane-1-sulfonic acid 4-[1-(2,4-dichlorophenyl)-3-methyl-4-oxo-5-piperidin-1-yl-4,5,6,7-tetrahydro-1H-pyrrolo[3,2-c]pyridine-2-yl]phenyl ester To a solution of 1-(2,4-dichlorophenyl)-2-(4-hydroxyphenyl)-3-methyl-5-piperidin-1-yl-1,5,6,7-tetrahydropyrrolo[3,2-c]pyridine-4-one (0.40 g, 0.85 mmol) in dichloromethane (20 ml) at 0° C. was added triethylamine (0.14 ml, 1.02 mmol) followed by 3,3,3-trifluoropropanesulfonyl chloride (0.20 g, 1.02 mmol). The reaction mixture was subsequently stirred at room temperature for two hours. Concentration and purification by flash chromatography (heptane:EtOAc gradient) afforded 200 mg (37%) of the title compound as a colorless solid.

$^1$H NMR ($CDCl_3$): δ 7.51 (1H, m), 7.34-7.02 (6H, m), 3.75 (2H, m), 3.53-3.44 (3H, m), 3.40-3.00 (2H, broad s), 2.87-2.60 (5 H, m), 2.41 (3H, s), 1.80-1.50 (6H, m), 1.40-1.20 (2H, m). MS: 630 (M+H). HPLC: 95%

Example 3

3,3,3-Trifluoropropane-1-sulfonic acid 4-[1-(2-chloro-4-fluorophenyl)-3-methyl-4-oxo-5-piperidin-1-yl-4,5,6,7-tetrahydro-1H-pyrrolo[3,2-c]pyridin-2-yl]phenyl ester Step 1  4-(2-Chloro-4-fluorophenylamino)-5,6,3',4',5',6'-hexahydro-2'H-[1,1']bipyridinyl-2-one

[1,1']-Bipiperidinyl-2,4-dione (2.00 g, 10.19 mmol) was dissolved in toluene (8 ml) and 2-chloro-4-fluorophenylamine (1.78 g, 12.23 mmol) was added. More toluene (5 ml) was added. The reaction mixture was boiled under reflux at 110° C. for 17 h then allowed to cool. When the reaction mixture reached rt the product precipitated and it was collected by filtration to yield a beige solid (1.80 g, 55%).

$^1$H-NMR (400 MHz, CDCl$_3$) δ 7.41-7.32 (1H, m), 7.18-7.09 (1H, m), 7.00-6.90 (1H, m), 5.51 (1H, s), 5.11 (1H, s), 3.54 (2H, t), 3.38-2.67 (4H, br), 2.57 (2H, t), 1.74-1.50 (4H, m), 1.43-1.30 (2H, m).

Step 2 3-{2-[4-(tert-Butyldimethylsilanyloxy)phenyl]-1-methyl-2-oxo-ethyl}-4-(2-chloro-4-fluorophenylamino)-5,6,3',4',5',6'-hexahydro-2'H-[1,1']bipydinyl-2-one NaH (0.15 g, 6.25 mmol) was placed in a flask under nitrogen and dry THF (5 ml) was added. The mixture was cooled to 0° C. with an icebath and 4-(2-chloro-4-fluorophenylamino)-5,6,3',4',5',6'-hexahydro-2'H-[1,1']bipyridinyl-2-one (0.70 g, 2.16 mmol) suspended in dry THF (8 ml) was added dropwise. After 1 h 40 min tetrabutylammonium iodide (0.085 g, 0.23 mmol) was added followed by dropwise addition of 2-bromo-1-[4-(tert-butyldimethylsilanyloxy)phenyl]propan-1-one (1.122 g, 3.27 mmol) dissolved in dry THF (2 ml). The icebath was removed after the last addition. The reaction was continued at rt for 4 h whereafter the reaction was quenched by adding phosphate buffer pH 7.0. The THF was evaporated. DCM/water were added and the phases separated. DCM was evaporated from the dried organic layer to yield the crude product as an orange solid (crude 1.135 g).

Step 3  2-[4-(tert-Butyldimethylsilanyloxy)phenyl]-1-(2-chloro-4-fluorophenyl)-3-methyl-5-piperidin-1-yl-1,5,6,7-tetrahydro-pyrrolo[3,2-c]pyridin-4-one 3-{2-[4-(tert-Butyldimethylsilanyloxy)phenyl]-1-methyl-2-oxo-ethyl}-4-(2-chloro-4-fluorophenylamino)-5,6,3',4',5',6'-hexahydro-2'H-[1,1']bipyridinyl-2-one (1.135 g, 1.94 mmol) was suspended in toluene (5 ml) and toluene-4-sulfonic acid (0.037 g, 0.19 mmol) was added. The reaction mixture was heated in a microwave oven at 100° C. for 30 min. Water/toluene were added to the reaction mixture and the phases separated. The organic phase was washed with water, dried (MgSO$_4$), filtered and evaporated to yield the crude product (crude 0.929 g).

Step 4 1-(2-Chloro-4-fluoro-phenyl)-2-(4-hydroxy-phenyl)-3-methyl-5-piperidin-1-yl-1,5,6,7-tetrahydro-pyrrolo[3,2-c]pyridin-4-one 2-[4-(tert-Butyldimethylsilanyloxy)phenyl]-1-(2-chloro-4-fluorophenyl)-3-methyl-5-piperidin-1-yl-1,5,6,7-tetrahydropyrrolo[3,2-c]pyridin-4-one (0.929 g, 1.63 mmol) was suspended in THF (10 ml) and TBAF (1 M in THF, 1.64 ml) was added. The reaction mixture was stirred at rt for 1 h whereafter the solvent was evaporated and ethyl acetate/water added. The phases were separated and the organic phase dried and evaporated. The crude product was recrystallised from ethyl acetate/toluene to yield the product as an orange solid (0.223 g, 23% over 3 steps).

Step 5  3,3,3-Trifluoropropane-1-sulfonic acid 4-[1-(2-chloro-4-fluorophenyl)-3-methyl-4-oxo-5-piperidin-1-yl-4,5,6,7-tetrahydro-1H-pyrrolo[3,2-c]pyridin-2-yl]phenyl ester 1-(2-Chloro-4-fluorophenyl)-2-(4-hydroxyphenyl)-3-methyl-5-piperidin-1-yl-1,5,6,7-tetrahydropyrrolo[3,2-c]pyridin-4-one (0.223 g, 0.49 mmol) was co-concentrated with pyridine twice and put under nitrogen. Pyridine (2.5 ml) was added and the reaction mixture cooled to 0° C. with an ice-bath followed by addition of 3,3,3-trifluoropropane-1-sulfonyl chloride (0.153 g, 0.78 mmol). The reaction mixture was stirred at 0° C. for 3 h adding more 3,3,3-trifluoropropane-1-sulfonyl chloride (0.171 g, 0.87 mmol) after 1 h 10 min. The ice bath was removed and the reaction mixture evaporated. The crude product was purified by hplc to yield the product as a beige solid after freeze-drying (0.19 g, 63%).

HRMS Calcd for $[C_{28}H_{28}ClF_4N_3O_4S+H]^+$: 614.150. Found: 614.150. $^1$H-NMR (400 MHz, CD$_3$OD), δ 7.33-7.25 (2H, m), 7.20-7.10 (4H, m), 7.08-7.01 (1H, m), 3.67-3.54 (4H, m), 3.10-2.67 (6H, m), 2.59 (2H, t), 2.22 (3H, s), 1.83-1.49 (4H, m), 1.49-1.19 (2H, m).

Example 4

1-(2-Chlorophenyl)-3-methyl-5-piperidin-1-yl-2-[4-(4,4,4-trifluorobutoxy)phenyl]-1,5,6,7-tetrahydropyrrolo[3,2-c]pyridine-4-one Potassium carbonate (0.19 g, 1.38 mmol) was added to a solution of 1-(2-chlorophenyl)-2-(4-hydroxyphenyl)-3-methyl-5-piperidin-1-yl-1,5,6,7-tetrahydropyrrolo[3,2-c]pyridine-4-one, from Ex. 1, Step 8 (0.50 g, 1.15 mmol) in DMF (30 ml) followed by 1-iodo-4,4,4-trifluorobutane (328 mg, 1.38 mmol). The reaction mixture was heated at 80° C. overnight. TLC showed very little conversion to starting material; 656 mg (2 eqv.) 1-iodo-4,4,4-trifluorobutane and 380 mg (2 eqv.) K$_2$CO$_3$ were added and heating continued for one hour. After cooling to rt, water was added and the product extracted with EtOAc (×3). The combined organic extracts were washed with brine (×2), dried (Na$_2$SO$_4$), filtered and concentrated. Flash chromatography (heptane:EtOAc gradient) afforded 250 mg (40%) of the title compound as a colorless solid.

$^1$H NMR (CDCl$_3$): δ 7.47 (1H, m), 7.34-7.18 (2H, m), 7.11-7.05 (3H, m), 6.74 3.75 (2H, m), 3.97 (2H, t), 3.73-3.70 (2H, broad t), 3.40-2.80 (4H, broad m), 2.74-2.61 (2H, m), 2.39-2.24 (5H, s and m), 2.07-2.00 (2H, m), 1.69-1.61 (4H, m), 1.48-1.46 (2H, m). MS: 568 (M+Na). HPLC: 97.5%

Example 5

3,3,3-Trifluoropropane-1-sulfonic acid 4-[1-(2,4-dichlorophenyl)-3-methyl-4-oxo-5-piperidin-1-yl-4,5-dihydro-1H-pyrrolo[3,2-c]pyridin-2-yl]phenyl ester Step 1 3-(Piperidin-1-ylamino)-propionic acid methyl ester To a solution of 1-aminopiperidine (100 g, 1.00 mol) in dry methanol at 0° C., methyl acrylate (99.0 ml, 1.10 mol) was added dropwise. The resulting mixture was stirred at room temperature overnight. After evaporation of the solvent, heptane was added to the residue, and the white solid (impurity) removed by filtration. The filtrate was concentrated to dryness to afford 80.0 g (43%) of the title compound as a yellow oil. Alternatively this reaction was performed at 50° C. using toluene as the solvent with a 0.7 molar excess of 1-aminopiperidine. Excess 1-aminopiperidine was removed from the residue by co-distillation with xylene, then toluene and then hexane.

Step 2 N-(2-Methoxycarbonylethyl)-N-piperidin-1-yl-maloamic acid ethyl ester

To a solution of 3-(piperidin-1-ylamino)propionic acid methyl ester (80.0 g, 0.43 mol) in dichloromethane was added triethylamine (71.0 ml, 0.50 mol) followed by slow addition of ethyl malonyl chloride (60.0 ml, 0.47 mol) at 0° C. The resulting slurry was stirred at room temperature for 4 hours. Water was added and the phases separated. The organic phase was dried ($Na_2SO_4$), filtered and concentrated. Flash chromatography (toluene:EtOAc 9:1-1:1) gave 81.0 g (63%) of the product as an oil used without further purification. Alternatively the reaction was performed using 2-methyltetrahydrofuran as the solvent and N-methylmorpholine as the base. The reaction was also performed with methyl malonyl chloride which gave N-(2-methoxycarbonylethyl)-N-piperidin-1-yl-maloamic acid methyl ester m.p. 54-57° C. which was used as an alternative in the next step.

Step 3 2,4-Dioxo-[1,1']bipiperidinyl-3-carboxylic acid ethyl ester

To a solution of N-(2-methoxycarbonylethyl)-N-piperidin-1-yl-maloamic acid ethyl ester (60.0 g, 0.20 mol) in a mixture of THF (1100 ml) and DMF (490 ml) was added cesium carbonate (195 g, 0.60 mol). The resulting mixture was boiled under reflux (80° C.) for 48 hours. The cooled reaction mixture was filtered and the filtrate evaporated. The combined filtered solid and the filtrate residue were purified by flash chromatography ($CH_2Cl_2$: MeOH 70:30) to give 15.0 g (28%) of the title compound as a pale yellow oil.

Alternatively the reaction was performed using toluene as the solvent and N-(2-methoxycarbonylethyl)-N-piperidin-1-yl-maloamic acid methyl ester and adding the base sodium methoxide in methanol (1.4 equivs) at below 10° C. then boiling under reflux for 1 hour. Concentration, addition of water and acidification to pH6 with conc. HCl produced 2,4-dioxo-[1,1']bipiperidinyl-3-carboxylic acid methyl ester m.p. 157-159° C. after filtration and washing with water. This methyl ester was used as an alternative in the next step.

Step 4 [1,1']Bipiperidinyl-2,4-dione

The ethyl ester product from step 3 was dissolved in 10% acetic acid (250 ml) and the solution boiled under reflux for one hour. The cooled reaction mixture was evaporated, and the residue purified by flash chromatography ($CH_2Cl_2$: acetone 9:1-1:1) to give 4.00 g (36%) of the title compound as a semi-solid.

Alternatively the methyl ester from step 3 was heated at reflux for 2 hours in a mixture of water (2 equivalents) and acetonitrile (10 volumes) at pH 3 (adjusted by addition of dilute HCl approx 5 M) and the product hydrochloride m.p. 89-90° C. purified by crystallisation from ethyl acetate/hexane.

Step 5 2-bromo-1-(4-hydroxyhenyl)propan-1-one

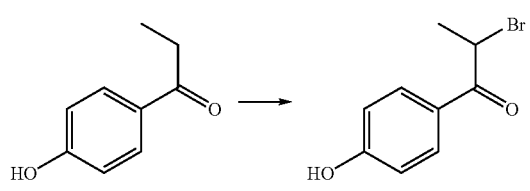

Acetic acid (25 ml) was added to 1-(4-hydroxyphenyl)propan-1-one (10.000 g, 66.587 mmol) and pyridine hydroperbromide (24.767 g, 69.916 mmol) at rt. The reaction mixture was stirred at rt for 3 h and 5 min. Water (110 ml) was added dropwise during 20 min and after 30 min of stirring more water (40 ml) was added during 5 min. The mixture was cooled to 0° C. and left at rt overnight. Solid material had formed in the reaction mixture which was collected by filtration, washed with water and dried under vacuum to yield the product as a solid (13.76 g, 90%).

$^1$H-NMR (400 MHz, $CDCl_3$), δ 7.96 (d, 2H), 6.91 (d, 2H), 5.25 (q, 1H), 1.87 (d, 3H). MS m/z 229 $(M+H)^+$.

Alternatively the reaction was performed by adding a mixture of 1-(4-hydroxyphenyl)-propan-1-one (1 equivalent) in ethyl acetate (5 volumes) to a mixture of ground $CuBr_2$ (2 equivs) in ethyl acetate (7.5 volumes) which was being boiled under reflux with vigorous stirring. After boiling for 4 hours the mixture was filtered at 60° C. through a filtration aid. The residue was washed with ethyl acetate and the filtrate and washings were treated with activated charcoal, filtered and evaporated to give the product.

Step 6 2-bromo-1-[4-(1-ethoxyethoxy)phenyl]propan-1-one

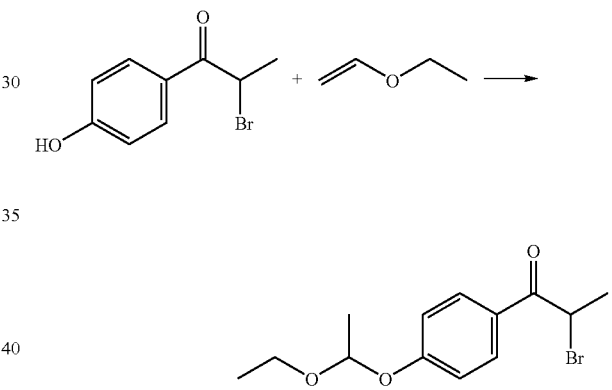

Ethoxyethene (3.148 g, 43.655 mmol) and TFA (0.249 g, 2.183 mmol) was added to a suspension of 2-bromo-1-(4-hydroxyphenyl)propan-1-one (5.000 g, 21.827 mmol) in toluene (50 ml) at rt. The reaction mixture was stirred at 30° C. for 2 h and 30 min. The solvent was evaporated to yield the product as an oil (6.83 g, 100%).

$^1$H-NMR (400 MHz, DMSO), δ 7.98 (d, 2H), 7.09 (d, 2H), 5.72 (q, 1H), 5.62 (q, 1H), 3.68-3.57 (m, 1H), 3.51-3.41 (m, 1H), 1.73 (d, 3H), 1.40 (d, 3H), 1.06 (t, 3H). MS m/z 301 $(M+H)^+$.

Step 7 4-[(2,4-dichlorophenyl)amino]-1-piperidin-1-yl-5,6-dihydropyridin-2(1H)-one

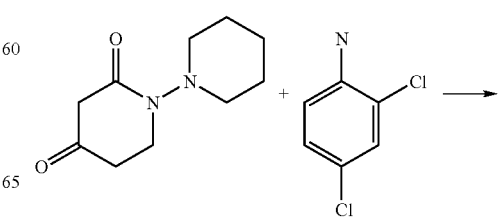

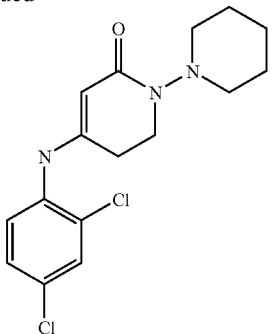

1,1'-bipiperidine-2, 4-dione (1,000 g, 4,739 mmol) and 2,4-dichloroaniline (0.921 g, 5.687 mmol) were dissolved in 2-methyltetrahydrofuran (10 ml) and the reaction mixture was boiled under reflux for 22 h whilst the water formed was removed using a Dean and Stark apparatus. Upon cooling to rt the product precipitated and was collected by filtration to yield a white solid (1.490 g, 92%).

MS m/z 340 (M+H)$^+$.

Step 8 4-[(2,4-dichlorophenyl)amino]-3-{2-[4-(1-ethoxyethoxy)phenyl]-1-methyl-2-oxoethyl}-1-piperidin-1-yl-5,6-dihydropyridin-2(1H)-one

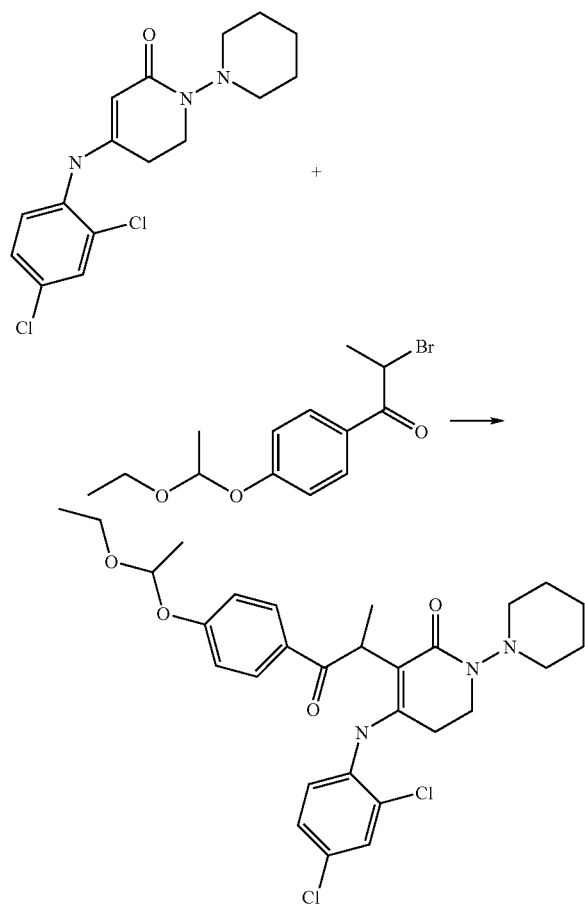

4-[(2,4-dichlorophenyl)amino]-1-piperidin-1-yl-5,6-dihydropyridin-2(1H)-one (450 mg, 1.323 mmol) suspended in THF (7 ml) was added during 15 min to NaH (67 mg, 2.645 mmol) suspended in THF (5 ml) at 5° C. under nitrogen. After the resulting mixture had been stirred at 0° C. for 1 h tetrabutylammonium iodide (49 mg, 0.132 mmol) was added followed by dropwise addition of 2-bromo-1-[4-(1-ethoxyethoxy)phenyl]propan-1-one (597 mg, 1.984 mmol) dissolved in THF (5 ml) during 15 min. After the addition the cooling bath was removed and the reaction was continued at rt overnight. Water was added and the solvent was removed by evaporation. The residue was partitioned between DCM and water. The organic phase was dried (MgSO$_4$), filtered and evaporated to yield an orange oil (1.030 g, 90%).

MS m/z 560 (M+H)$^+$.

Step 9 1-(2,4-dichlorophenyl)-2-(4-hydroxyphenyl)-3-methyl-5-piperidin-1-yl-1,5,6,7-tetrahydro-4H-pyrrolo[3,2-c]pyridin-4-one

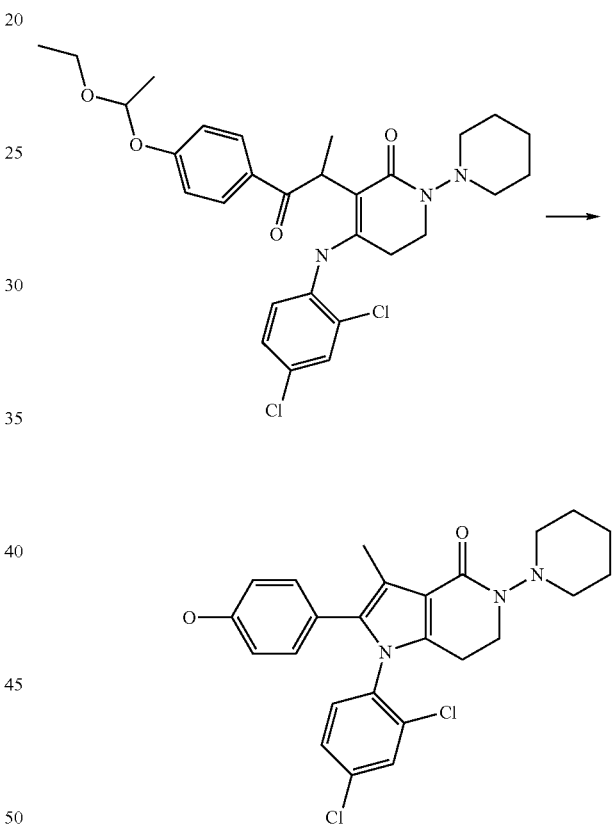

TFA (22 mg, 0.194 mmol) was added to 4-[(2,4-dichlorophenyl)amino]-3-{2-[4-(1-ethoxyethoxy)phenyl]-1-methyl-2-oxoethyl}-1-piperidin-1-yl-5,6-dihydropyridin-2(H)-one (1.090 g, 1.945 mmol) dissolved in toluene (15 ml) under nitrogen. The reaction mixture was stirred at 60° C. for 2 h, adding more TFA (89 mg, 0.778 mmol) after 50 min.

When the mixture had reached rt the product was collected by filtration and recrystallised from methanol to yield a beige solid (0.560 g, 55%).

$^1$H-NMR (400 MHz, DMSO), δ 9.59-9.28 (br, 1H), 7.72 (d, 1H), 7.43 (dd, 1H), 7.37 (d, 1H), 6.82 (d, 2H), 6.59 (d, 2H), 3.62-3.54 (m, 2H), 3.27-2.90 (br, 4H), 2.61-2.43 (m, 2H), 2.12 (s, 3H), 1.61-1.45 (br, 4H), 1.39-1.24 (br, 2H). MS m/z 470 (M+H)$^+$.

Step 10 1-(2,4-dichlorophenyl)-2-(4-hydroxyphenyl)-3-methyl-5-piperidin-1-yl-1,5-dihydro-4H-pyrrolo[3,2-c]pyridin-4-one

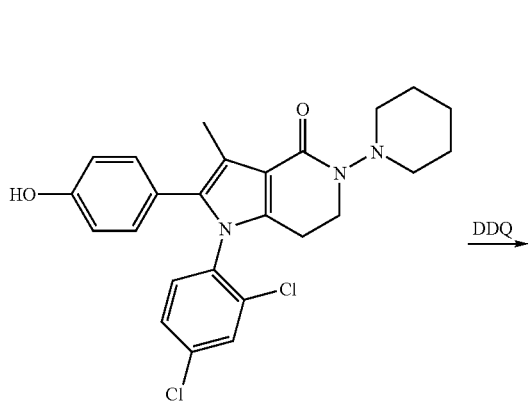

A suspension of 1-(2,4-dichlorophenyl)-2-(4-hydroxyphenyl)-3-methyl-5-piperidin-1-yl-1,5,6,7-tetrahydro-4H-pyrrolo[3,2-c]pyridin-4-one (153 mg, 0.325 mmol) and DDQ (295 mg, 1.301 mmol) in 1,4-dioxane (12 ml) was stirred at rt for 1 h and 20 min followed by 1 h and 50 min at 35° C. and 2 h and 50 min at 45° C. The solvent was evaporated and the product purified by hplc. The solvent was evaporated and water added. The product was extracted from the water phase with DCM and EtOAc. The combined organic phases were evaporated and the residue was re-suspended in toluene and evaporated to yield the product as a yellow solid (74 mg, 49%). MS m/z 468 (M+H)$^+$.

Step 11 3,3,3-Trifluoropropane-1-sulfonic acid 4-[1-(2,4-dichlorophenyl)-3-methyl-4-oxo-5-piperidin-1-yl-4,5-dihydro-1H-pyrrolo[3,2-c]pyridin-2-yl]phenyl ester

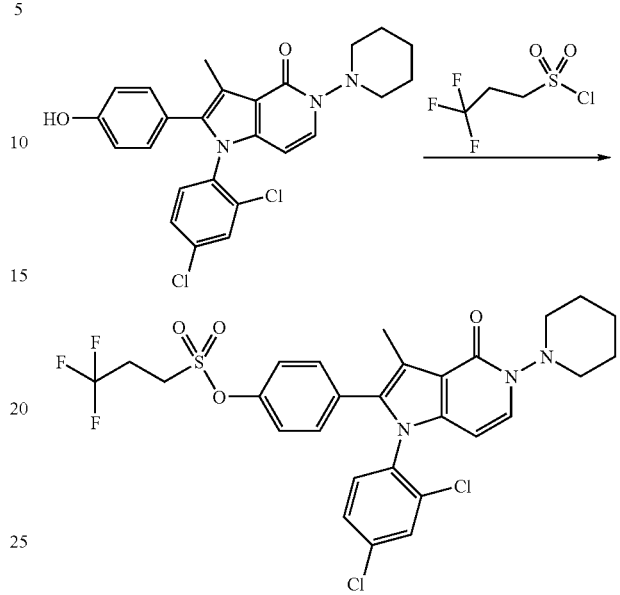

3,3,3-Trifluoro-propane-1-sulfonyl chloride (100 mg, 0.509 mmol) was added to 1-(2,4-dichlorophenyl)-2-(4-hydroxyphenyl)-3-methyl-5-piperidin-1-yl-1,5-dihydro-4H-pyrrolo[3,2-c]pyridin-4-one (74 mg, 0.158 mmol) dissolved in pyridine (5 ml) at 0° C. The reaction was continued at 0° C. for 1 h and 15 min and then at rt. After 15 min at rt more 3,3,3-trifluoro-propane-1-sulfonyl chloride (260 mg, 1.323 mmol) was added. After 15 min the solvent was evaporated. Purified by flash chromatography (20-100% EtOAc in toluene) to yield the title compound as a white solid after evaporation (24 mg, 24%).

$^1$H-NMR (400 MHz, CDCl$_3$), δ 7.47 (d, 1H), 7.25-7.12 (m, 6H), 7.06 (d, 1H), 5.72 (d, 1H), 4.02-3.89 (m, 2H), 3.47-3.41 (m, 2H), 3.12-2.95 (m, 2H), 2.83-2.68 (m, 2H), 2.53 (s, 3H), 1.70-1.50 (m, 4H), 1.46-1.18 (m, 2H). HRMS Calcd for [C$_{28}$H$_{26}$Cl$_2$F$_3$N$_3$O$_4$S+H]$^+$: 628.105. Found: 628.107.

Example 6

3,3,3-Trifluoropropane-1-sulfonic acid 4-[1-(2-chloro-4-fluorophenyl)-3-methyl-4-oxo-5-piperidin-1-yl-4,5-Dihydro-1H-pyrrolo[3,2-c]pyridin-2-yl] phenyl ester

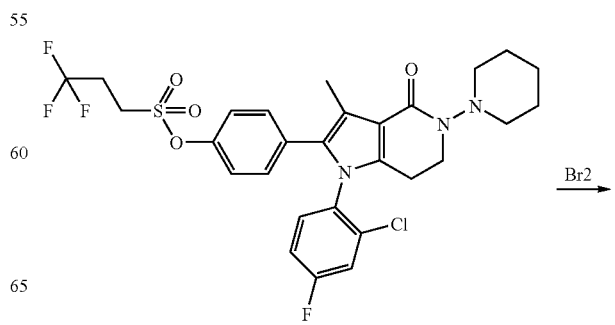

-continued

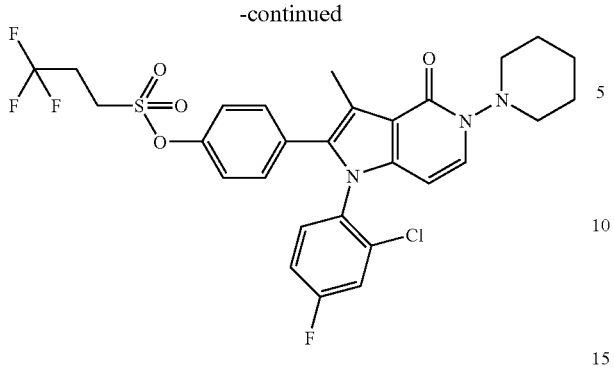

Bromine (39.0 mg, 0.244 mmol) dissolved in acetic acid (0.556 ml) was added to a solution of 4-[1-(2-chloro-4-fluorophenyl)-3-methyl-4-oxo-5-piperidin-1-yl-4,5,6,7-tetrahydro-1H-pyrrolo[3,2-c]pyridin-2-yl]phenyl 3,3,3-trifluoropropane-1-sulfonate (75 mg, 0.122 mmol) (Example 3) in THF (3 ml) at −78° C. After 30 min at −78° C. the reaction mixture was allowed to reach rt. After 3 h at rt more bromine (19.5 mg, 0.122 mmol) dissolved in acetic acid (0.278 ml) was added and the reaction continued at rt for 5 h before the solvent was removed by evaporation. Purified by hplc to yield the title compound as a solid (22 mg, 29%).

$^1$H-NMR (400 MHz, CDCl$_3$), δ 7.25-7.07 (m, 7H), 7.00-6.92 (m, 1H), 5.73 (d, 1H), 4.00-3.87 (m, 2H), 3.46-3.38 (m, 2H), 3.10-2.96 (m, 2H), 2.81-2.67 (m, 2H), 2.52 (s, 3H), 1.85-1.70 (m, 4H), 1.46-1.26 (m, 2H). MS m/z 612 (M+H)$^+$.

The following compounds are prepared in a similar manner to those described above:

Example 7

3,3,3-Trifluoropropane-1-sulfonic acid 4-[1-(2-chlorophenyl)-5-(2-hydroxy-cyclohexyl)-3-methyl-4-oxo-4,5,6,7-tetrahydro-1H-pyrrolo[3,2-c]pyridin-2-yl]phenyl ester Example 8

3,3,3-Trifluoropropane-1-sulfonic acid 4-[1-(2,4-dichlorophenyl)-5-(2-hydroxycyclohexyl)-3-methyl-4-oxo-4,5,6,7-tetrahydro-1H-pyrrolo[3,2-c]pyridin-2-yl]phenyl ester Example 9

3,3,3-Trifluoropropane-1-sulfonic acid 4-[1-(2-chlorophenyl)-5-(3-hydroxy-cyclohexyl)-3-methyl-4-oxo-4,5,6,7-tetrahydro-1H-pyrrolo[3,2-c]pyridin-2-yl]phenyl ester Example 10

3,3,3-Trifluoropropane-1-sulfonic acid 4-[1-(2-chloro-phenyl)-5-cyclohexyl-3-methyl-4-oxo-4,5,6,7-tetrahydro-1H-pyrrolo[3,2-c]pyridin-2-yl]phenyl ester Example 11

3,3,3-Trifluoropropane-1-sulfonic acid 4-[1-(2,4-dichlorophenyl)-5-(2-hydroxycyclohexyl)-3-methyl-4-oxo-4,5-dihydro-1H-pyrrolo[3,2-c]pyridin-2-yl] phenyl ester Example 12

3,3,3-Trifluoropropane-1-sulfonic acid 4-[1-(2-chlorophenyl)-5-cyclohexyl-3-hydroxymethyl-4-oxo-4,5,6,7-tetrahydro-1H-pyrrolo[3,2-c]pyridin-2-yl]phenyl ester Example 13

3,3,3-Trifluoropropane-1-sulfonic acid 4-[1-(2-chlorophenyl)-5-cyclohexyl-3-hydroxymethyl-4-oxo-4,5-dihydro-1H-pyrrolo[3,2-c]pyridin-2-yl]phenyl ester Example 14

3,3,3-Trifluoropropane-1-sulfonic acid 4-[1-(2-chlorophenyl)-5-(2-hydroxy-cyclohexyl)-3-hydroxymethyl-4-oxo-4,5-dihydro-1H-pyrrolo[3,2-c]pyridin-2-yl]phenyl ester Example 15

3,3,3-Trifluoropropane-1-sulfonic acid 4-(3-methyl-4-oxo-5-piperidin-1-yl-1-o-tolyl-4,5,6,7-tetrahydro-1H-pyrrolo[3,2-c]pyridin-2-yl)phenyl ester Example 16

1-(2,4-Dichlorophenyl)-3-methyl-5-piperidin-1-yl-2-[4-(4,4,4-trifluoro-butoxy)-phenyl]-1,5,6,7-tetrahydropyrrolo[3,2-c]pyridin-4-one.

It will be appreciated by those skilled in the art that the compounds of the invention may be named as 1,5,6,7-tetrahydro-1H-pyrrolo[3,2-c]pyridines or may be named as 4,5,6,7-tetrahydro-1H-pyrrolo[3,2-c]pyridines.

General Synthetic Route 1
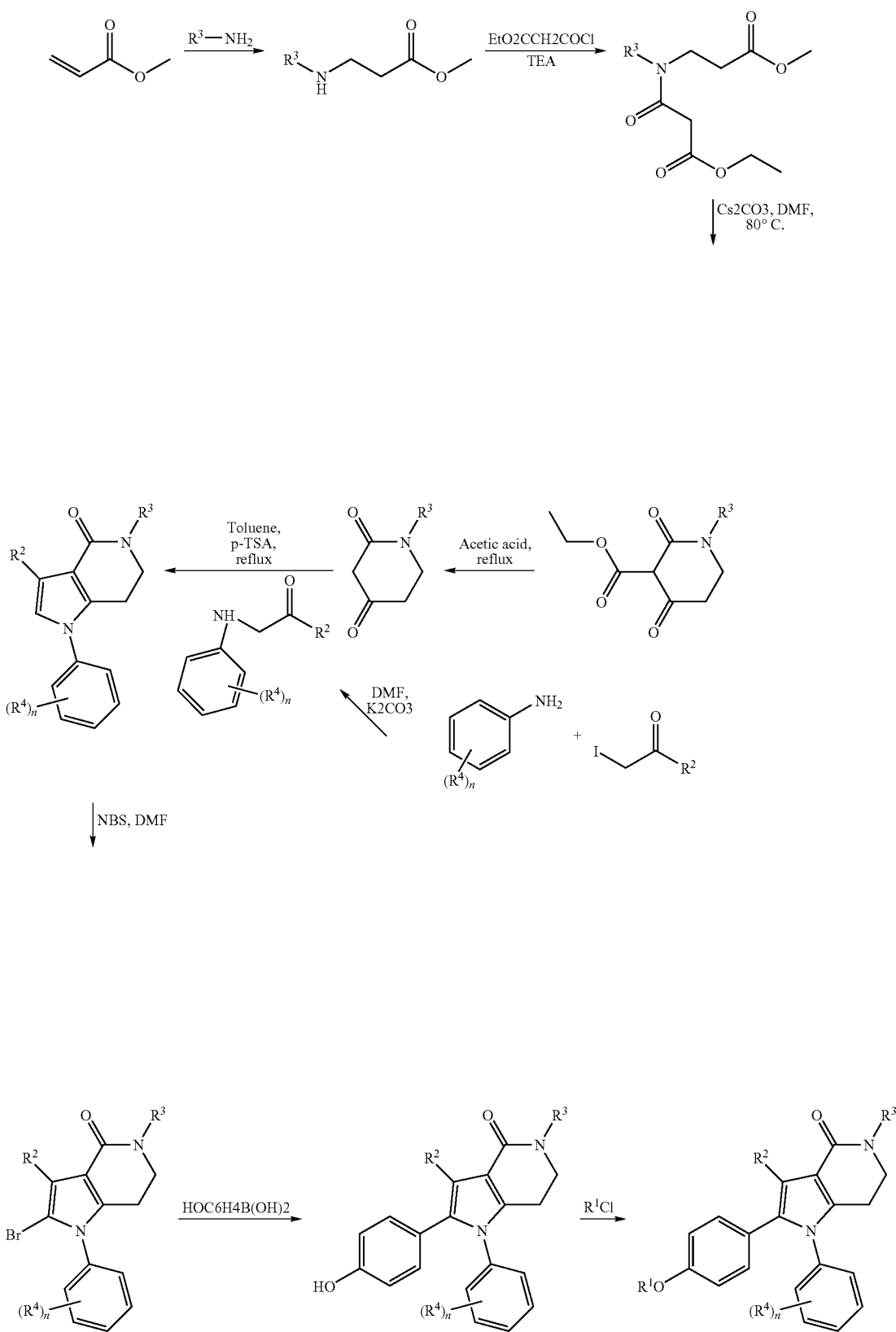

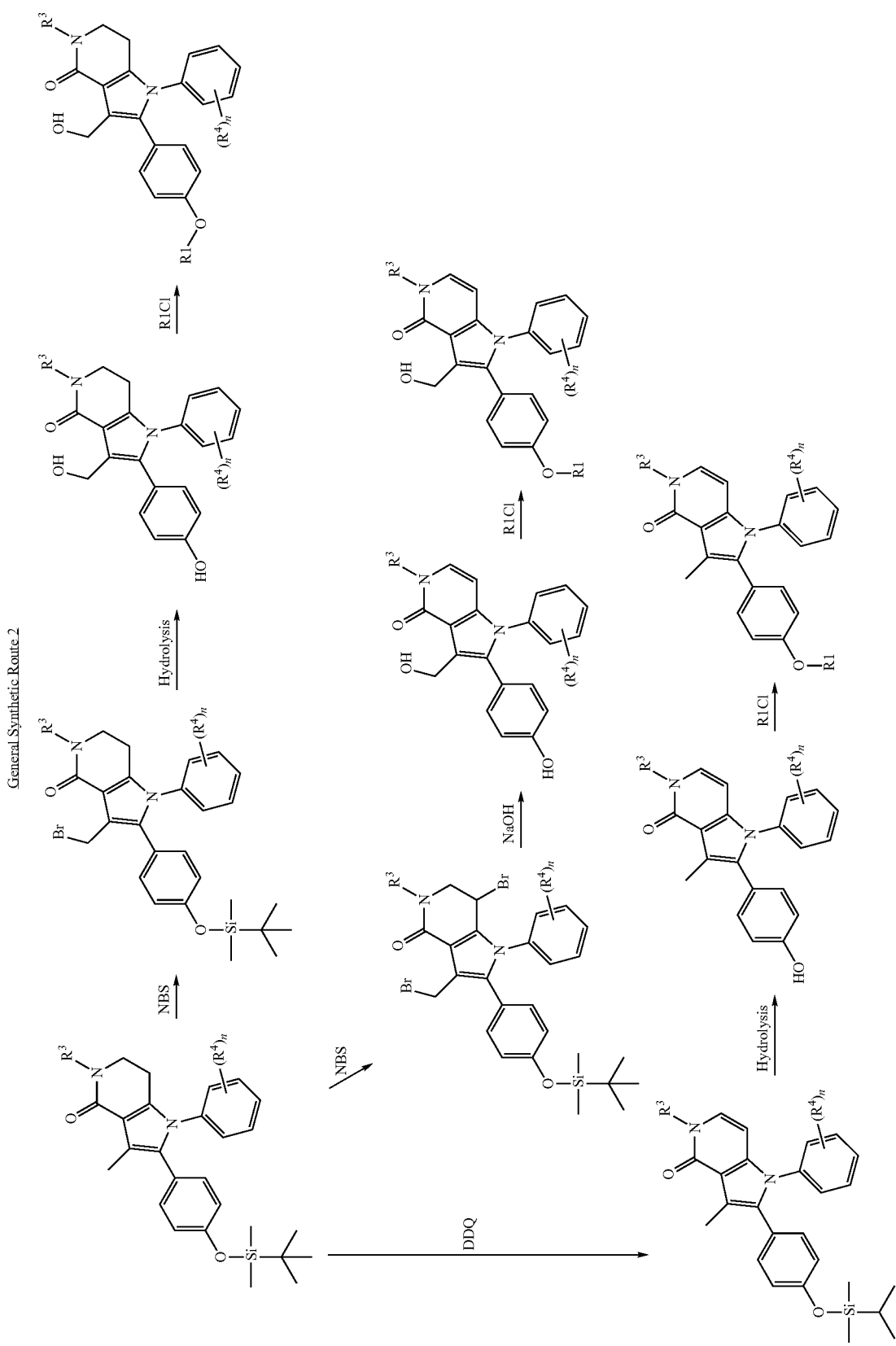

General Synthetic Route 3
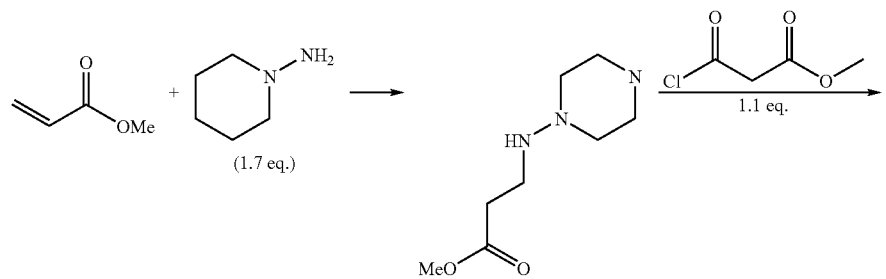
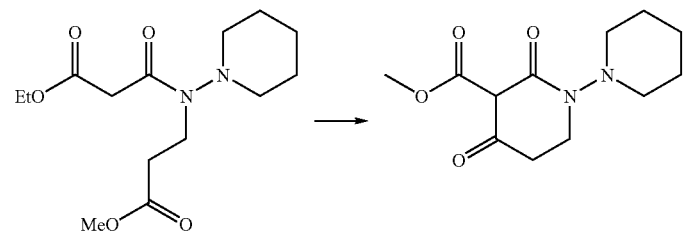
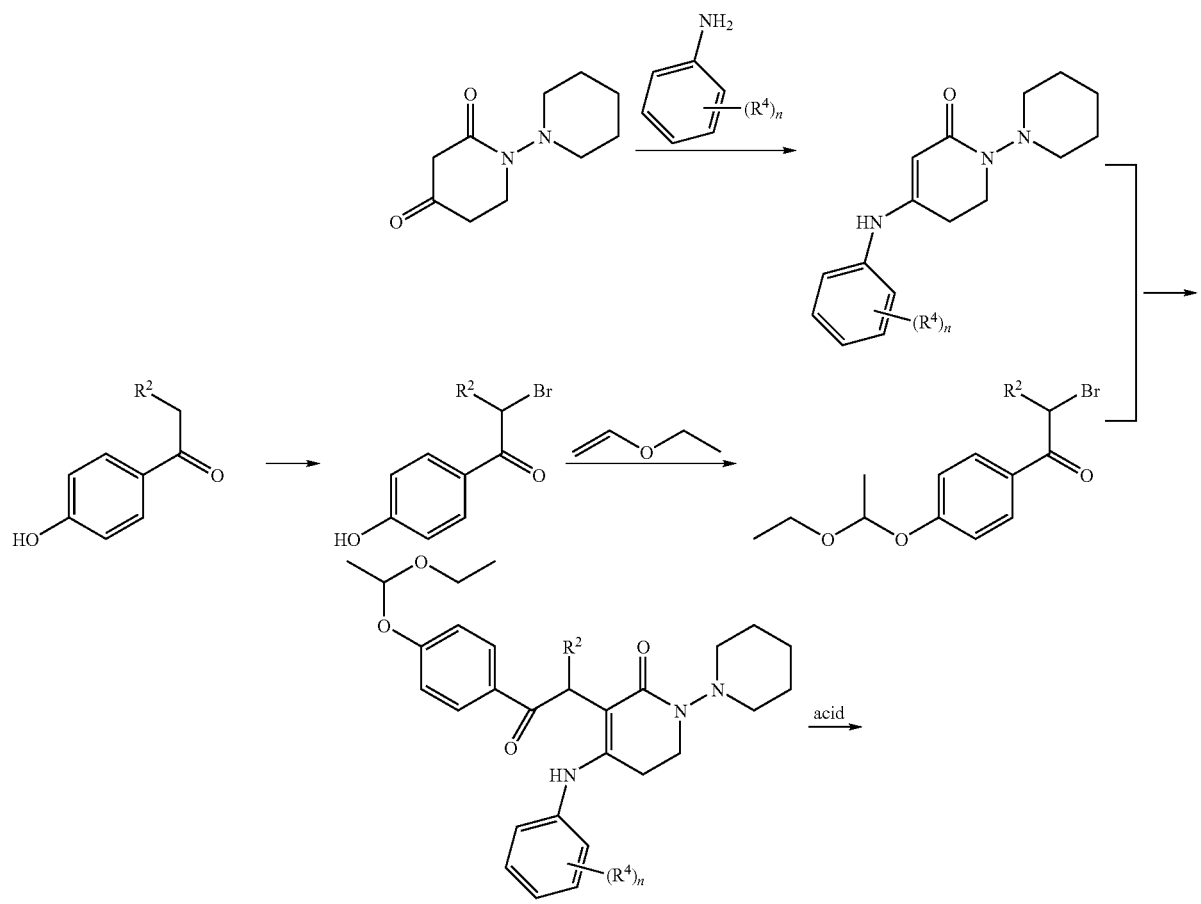

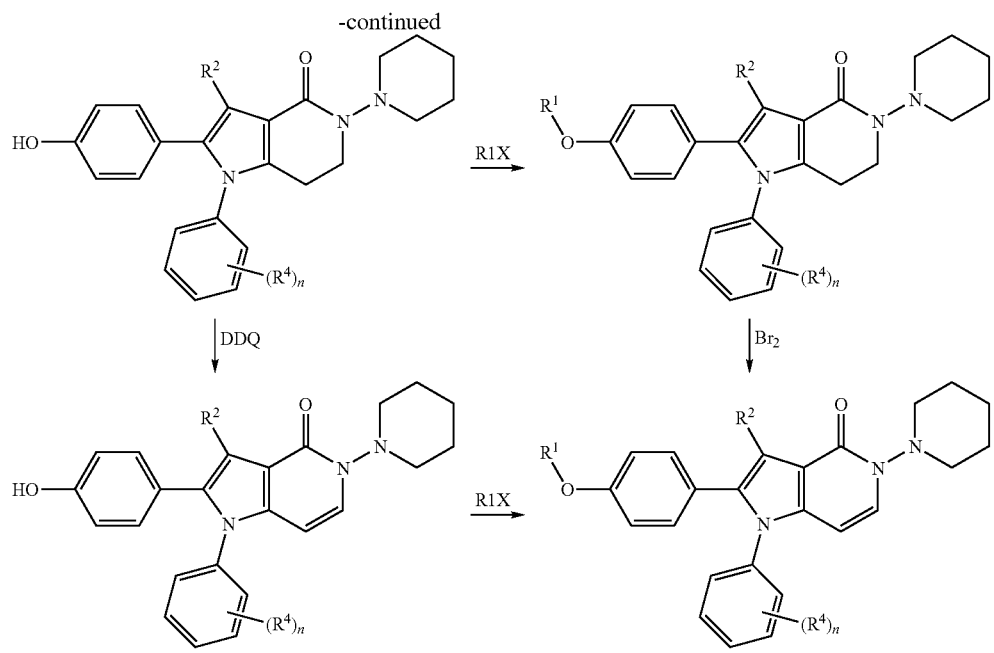

What is claimed is:

1. A compound selected from the group consisting of:
3,3,3-trifluoropropane-1-sulfonic acid 4-[1-(2,4-dichlorophenyl)-3-methyl-4-oxo-5-piperidin-1-yl-4,5-dihydro-1H-pyrrolo[3,2-c]pyridin-2-yl]phenyl ester; and
3,3,3-trifluoropropane-1-sulfonic acid 4-[1-(2-chloro-4-fluorophenyl)-3-methyl-4-oxo-5-piperidin-1-yl-4,5-dihydro-1H-pyrrolo[3,2-c]pyridin-2-yl]phenyl ester
or a pharmaceutically acceptable salt thereof.

2. A pharmaceutical formulation comprising a compound as claimed in claim 1 and a pharmaceutically acceptable adjuvant, diluent or carrier.

3. A method of treating obesity, comprising administering a pharmacologically effective amount of a compound as claimed in claim 1, or a pharmaceutically acceptable salt thereof, to a patient in need thereof.

* * * * *